United States Patent
Karunanithi et al.

(10) Patent No.: US 11,355,227 B2
(45) Date of Patent: Jun. 7, 2022

(54) ACTIVITY CAPABILITY MONITORING

(71) Applicant: Commonwealth Scientific and Industrial Research Organisation, Acton (AU)

(72) Inventors: Mohanraj Krishnamoorthy Karunanithi, Acton (AU); Qing Zhang, Acton (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 17/018,756

(22) Filed: Sep. 11, 2020

(65) Prior Publication Data
US 2021/0241878 A1    Aug. 5, 2021

Related U.S. Application Data

(63) Continuation of application No. 15/760,129, filed as application No. PCT/AU2016/050858 on Sep. 14, 2016, now abandoned.

(51) Int. Cl.
*G16H 20/30* (2018.01)
*A61B 5/11* (2006.01)
(Continued)

(52) U.S. Cl.
CPC .......... *G16H 20/30* (2018.01); *A61B 5/0022* (2013.01); *A61B 5/1113* (2013.01);
(Continued)

(58) Field of Classification Search
CPC ........ G16H 20/30; G16H 40/67; A61B 5/742; A61B 5/7282; A61B 5/1116;
(Continued)

(56) References Cited

U.S. PATENT DOCUMENTS 6,108,685 A    8/2000  Kutzik et al.
8,184,001 B2   5/2012  Kuris et al.
(Continued)

FOREIGN PATENT DOCUMENTS

GB    2 352 815 A    2/2001

OTHER PUBLICATIONS

Hussain et al., "Monitoring user activities in smart home environments," Inf Syst Front, 11 pages (2008).
(Continued)

*Primary Examiner* — Kerri L McNally
(74) *Attorney, Agent, or Firm* — Foley & Lardner LLP

(57) ABSTRACT

A method of monitoring activity capabilities of a subject, including determining sensor data for each of a plurality of sensors, the sensors being positioned within a living environment of the subject and the sensor data being indicative of activities performed by the subject; for each of a plurality of activity domains, determining a domain score indicative of a level of activity within the respective activity domain, the domain score being determined using sensor data from a respective combination of sensors within the respective domain; determining a reference activity level using reference domain scores during a reference time period; determining a current activity level using current domain scores during a monitoring time period; and generating an activity indicator in accordance with the current activity level and the reference activity level, the activity indicator being indicative of differences between the current activity level and the reference activity level, thereby providing feedback on the activity capabilities of the subject.

18 Claims, 17 Drawing Sheets

(51) Int. Cl.
- *A61B 5/00* (2006.01)
- *G06Q 10/06* (2012.01)
- *G16H 40/67* (2018.01)

(52) U.S. Cl.
CPC ........... *A61B 5/1116* (2013.01); *A61B 5/1118* (2013.01); *A61B 5/7246* (2013.01); *A61B 5/7282* (2013.01); *A61B 5/742* (2013.01); *A61B 5/746* (2013.01); *G06Q 10/06* (2013.01); *G06Q 10/0639* (2013.01); *G16H 40/67* (2018.01); *A61B 2503/08* (2013.01); *A61B 2560/0252* (2013.01)

(58) Field of Classification Search
CPC ..... A61B 5/1118; A61B 5/1113; A61B 5/746; A61B 5/7246; A61B 5/0022; A61B 2503/08; A61B 2560/0252; G06Q 10/06; G06Q 10/0639
See application file for complete search history.

(56) References Cited

U.S. PATENT DOCUMENTS

| | | | |
|---|---|---|---|
| 8,798,573 | B2 | 8/2014 | Denning et al. |
| 8,810,388 | B2 | 8/2014 | Jacobs et al. |
| 2005/0234310 | A1 | 10/2005 | Alwan et al. |
| 2008/0001735 | A1 | 1/2008 | Tran |
| 2010/0302041 | A1* | 12/2010 | Malik ............... G08B 21/04 340/573.1 |
| 2011/0260871 | A1 | 10/2011 | Karkowski |
| 2012/0083705 | A1 | 4/2012 | Yuen et al. |
| 2012/0259245 | A1 | 10/2012 | Receveur |
| 2013/0141235 | A1 | 6/2013 | Utter, II |
| 2013/0216989 | A1 | 8/2013 | Cuthbert |
| 2014/0278139 | A1 | 9/2014 | Hong et al. |
| 2014/0281650 | A1 | 9/2014 | Gilbert et al. |
| 2015/0119760 | A1 | 4/2015 | Wisbey et al. |
| 2015/0120025 | A1 | 4/2015 | Wisbey et al. |
| 2018/0254096 | A1 | 9/2018 | Karunanithi et al. |

OTHER PUBLICATIONS

Office Action dated Dec. 9, 2019, in U.S. Appl. No. 15/760,129 (US 2018-0254096).

Office Action dated Feb. 14, 2019, in U.S. Appl. No. 15/760,129 (US 2018-0254096).

Office Action dated May 11, 2020, in U.S. Appl. No. 15/760,129 (US 2018-0254096).

Office Action dated May 28, 2019, in U.S. Appl. No. 15/760,129 (US 2018-0254096).

* cited by examiner

ACTIVITY CAPABILITY MONITORING

CROSS-REFERENCE TO RELATED APPLICATIONS

The present application a continuation of U.S. application Ser. No. 15/760,129, filed Mar. 14, 2018, which is the U.S. National Stage of International Application PCT/AU2016/050858, filed Sep. 14, 2016, which claims priority from Australian Patent Application 2015903753, filed Sep. 15, 2015.

BACKGROUND OF THE INVENTION

The present invention relates to a method and apparatus for monitoring activity capabilities of an individual, for example to determine the ability of an individual to perform activities of daily living.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Activity of Daily Living (ADL) has become the de facto clinical standard to assess the functional status of older people to be able live safely and independently in their home. Over past forty years, more than forty different ADL indexes have been developed to determine fundamental functional disability status of both patients and population. Measures of functional ability outlined by the ADL have become routine in the assessment of functional status of older people and believed to be a good predictor of a wide range of health-related behaviour in seniors.

Among them, the Katz ADL scale is a tool for assessing an older adult's ability to bathe, dress, use the toilet, transfer, remain continent, and feed her/himself. It's also used for evaluating changes in response to illness. The Katz index is easy to use and adaptable to most clinical assessment. ADL scales have also been widened to assessment that accommodate more sophisticated functional requirements full range of activities necessary for independent living such as ability to cope with financial transactions, neurological disorders and cognitive impairment prevalent with aging.

The current approach to measuring ADL is in a clinical setting prior to discharge from rehabilitation, for example by a clinician such as an occupational health therapist. In some cases, the discharge may be delayed (hence, increased length of stay) if modifications of the patient's home environment may be required to be done to adjust for their limited functional ability. Some form of ADL is also used in geriatric assessment for eligibility to residential care, which is again performed in a similar manner by a clinician or the like, in a clinical environment. However, this approach suffers from a number of drawbacks.

Firstly, it is not representative of an individual's living environment, and doesn't therefore necessarily take into account the individual's everyday living routines of activities. Secondly, it is subjective measure due to it being based on a clinical staff's observation and corresponding self-reported responses from the individual in question, and can therefore vary between assessors and individuals, meaning the outcomes are not objective or consistent. There is also evidence showing variations in ADL assessment, with results likely to be skewed by self-reported questions being interpreted differently due to individuals from various culture, language, and education backgrounds. Similar issues arise due to communication barriers from cognitive impairment having significant implications on achieving reliable ADL assessment. Thirdly, current assessments are clinically resource intensive, particularly from a home setting, making them impractical for long term care of the elderly or disabled populations. Fourthly, ADL can vary over time and therefore not practical to provide regular ADL assessment by a clinician.

Attempts have been made to implement sensing systems to reduce workload and provide more objective assessment. However, the majority of these systems still rely on assessment in a clinical setting and are not therefore reflective of actual typical activities performed by the individual. Additionally, such systems often rely on wearable sensors, which have the drawback of being intrusive and requiring compliance by the individual, for example in ensuring they wear the sensor. Other systems tend to focus on limited aspect of living, and do not objectively assess a complete range of tasks performed by the individual.

GB-2,352,815 describes an equipment monitor which is capable of learning how to respond to particular inputs (e.g. a neural network) is connected to a plurality of instruments (e.g. medical instruments in an intensive care ward or instruments in an industrial plant). During an initial training session, a human supervisor monitors the instruments to ensure that no potential alarm condition is encountered whilst the monitor assimilates the gamut of sensor data representative of "safe" or "healthy" conditions. Thereafter the equipment is left to sensor data an alarm if the collection of sensor data it is monitoring strays out of the range encountered during the training session. A button may be provided for indicating to the monitor that responses which give rise to false alarms should be included in its "safe" responses. The monitor may be provided with some rules prior to its learning phase.

However, this is focussed on fall detection and is not applicable more broadly to other aspects of activity capability assessment, or assessing a gradual decline in capabilities.

US2014/0281650 describes a passive monitoring system for use in a residential independent living framework. In some exemplary embodiments, the system may be used to alert a primary caregiver of a possible decline or change in an activity of daily living ("ADL") of the monitored individual. The system may collect usage data associated with, for example, electrical devices at the living quarters of the monitored individual. The collected data may include data pairs of time samples and voltage data associated with one or more electrical devices that the monitored individual is expected to utilize. Applying various filters to the collected data, a possible decline or change in ADL of the monitored individual may be identified.

However, this system focusses only on electrical device usage and is not applicable more broadly to activities that do not use electrical devices, as is the case with many activities of daily living.

U.S. Pat. No. 8,810,388 relates to a system and method for monitoring the location, movement and health of one or more individuals within an environment by a monitoring individual, such as a care giver. The system used includes optional monitoring devices including a wireless transceiver, access point devices including a wireless transceiver, a hub access point device including a wireless transceiver, and a local computing device. The system is programmed such that it has the capability to operate with or without the measure of time of flight value from the optional monitoring devices such that the system has the capability of monitoring the location, movement and health of an individual whether or not the individual is wearing the monitoring device.

However, this system is limited to movement monitoring and provides no guidance regarding capability to perform activities more broadly.

U.S. Pat. No. 8,184,001 describes a wireless contextual prompting device that provides contextual (context-aware) prompting in the home for applications such as Activities of Daily Living (ADL) monitoring, medication adherence, journaling, social messaging and coaching. The device combines the advantages of a small, wireless, battery-operated sensor that may be easily mounted at critical places in a person's daily routine with a low-power, high-contrast display panel that may be palm sized. The context may be displayed on the display screen as images, icons and/or text such that it is easy to interpret warnings by the young, elderly, or the language-challenged.

However, this arrangement focusses on providing prompting to individual's to assist them with performing tasks, which in many cases is intrusive, and does not objectively assess the individual's ability to perform the task.

U.S. Pat. No. 8,798,573 describes a monitoring system capable of monitoring the Activities of Daily Living (ADL) of one or more persons occupying a building. The monitoring system includes an information handling system having a radio-frequency (RF) scanner capable of scanning the RF ambient environment of the building. When an individual uses devices in the building that emit RF sensor data or emissions, the RF sensor data are detected by the RF scanner and analyzed by the information handling system. The characteristics of the detected RF sensor data are compared to a database of signature of known devices. If a detected RF sensor data matches the signature of a known device, the use of the device is logged into a database for ADL analysis.

This suffers from the drawback of being solely focused on RF sensor data detection and provides limited ability to detect a wide range of activities.

US2005/0234310 describes a method and related system to, among other things, automatically infer answers to all of the ADL questions and the first four questions of the IADL in the home. The inference methods detect the relevant activities unobtrusively, continuously, accurately, objectively, quantifiably and without relying on the patient's own memory (which may be fading due to aging or an existing health condition, such as Traumatic Brain Injury (TBI)) or on a caregiver's subjective report. The methods rely on the judicious placement of a number of sensors in the subject's place of residence, including motion detection sensors in every room, the decomposition of each relevant activity into the sub-tasks involved, identification of additional sensors required to detect the relevant sub-tasks and spatial-temporal conditions between the sensor data of sensors to formulate the rules that will detect the occurrence of the specific activities of interest. The sensory data logged on a computing device (computer, data logger etc.), date and time stamped, is analyzed using specialist data analysis software tools that check for the applicable task/activity detection rules. The methods are particularly useful for the continued in-home assessment of subjects living alone to evaluate their progress in response to medical intervention drug or physical therapy or decline in abilities that may be the indicator of the onset of disease over time. Measuring the frequency of each activity, the time required to accomplish an activity or a subtask and the number of activities/subtasks performed continuously over time can add extremely valuable quantification extensions to the existing ADL and IADL evaluation instruments, as it will not only reveal important information setting up a baseline for activity levels for each activity, but will also easily allow the detection of any drift from these personalized norms.

However, this requires a rules based approach, which is complex and prone to error in the event that rules are not suitable for a given circumstance. Furthermore, the document only describes the use of yes/no answers in assessing specific limited activities, which provides limited feedback in terms of quantifying abilities of an individual, and health status more generally.

SUMMARY OF THE PRESENT INVENTION

In one broad form the present invention seeks to provide a method of monitoring activity capabilities of a subject, the method including, in at least one processing device:
a) determining sensor data indicative of sensor readings for each of a plurality of sensors, the sensors being positioned within a living environment of the subject and the sensor data for each sensor being at least partially indicative of one or more activities performed by the subject;
b) for each of a plurality of activity domains, determining a domain score indicative of a level of activity within the respective activity domain, the domain score being determined using sensor data from a respective combination of sensors associated with the respective domain;
c) determining a reference activity level using reference domain scores measured during a reference time period;
d) determining a current activity level using current domain scores measured during a monitoring time period; and,
e) generating an activity indicator at least partially in accordance with the current activity level and the reference activity level, the activity indicator being at least partially indicative of differences between the current activity level and the reference activity level, thereby providing feedback on the activity capabilities of the subject.

In one broad form the present invention seeks to provide apparatus for monitoring activity capabilities of a subject, the apparatus including:
a) a plurality of sensors, the sensors being positioned within a living environment of the subject; and,
b) at least one processing device that:
i) determines sensor data indicative of sensor readings for each of a plurality of sensors, the sensors being positioned within a living environment of the individual and the sensor data for each sensor being at least partially indicative of one or more activities performed by the individual;
ii) for each of a plurality of activity domains, determines a domain score indicative of a level of activity within the respective activity domain, the domain score being determined using sensor data from a respective combination of sensors associated with the respective domain;
iii) determines a reference activity level using reference domain scores measured during a reference time period;

iv) determines a current activity level using current domain scores measured during a monitoring time period; and, v) generates an activity indicator at least partially in accordance with the current activity level and the reference activity level, the activity indicator being at least partially indicative of differences between the current activity level and the reference activity level, thereby providing feedback on the activity capabilities of the subject.

Typically the method includes:
a) determining an activity level score by combining the domain scores;
b) determining the reference activity level using the activity level score measured during the reference time period; and,
c) determining the current activity level using the activity level score measured during the monitoring time period.

Typically the combination includes at least one of:
a) a sum; and,
b) a weighted sum.

Typically the method includes:
a) determining an activity pattern indicative of relative values of domain scores;
b) determining the reference activity level using the activity pattern measured during the reference time period; and,
c) determining a current activity level using a current activity pattern measured during the monitoring time period.

Typically the method includes:
a) comparing the current activity level to the reference activity level; and,
b) generating the activity indicator at least partially in accordance with results of the comparison.

Typically the method includes comparing at least one of:
a) each current domain score to an equivalent reference domain score;
b) each current domain score to a respective reference range derived from an equivalent reference domain score;
c) a current activity level score to a reference activity level score;
d) a current activity level score to a respective reference range derived from a reference activity level score;
e) a current activity pattern to a reference activity pattern; and,
f) a current activity level to a reference activity level measured during a corresponding time period.

Typically the method includes:
a) determining a condition suffered by the subject; and,
b) determining, at least partially in accordance with the condition, at least one of:
  i) an activity level score;
  ii) a domain score;
  iii) a reference domain score range; and,
  iv) a reference activity level range.

Typically the method includes:
a) determining an action rule; and,
b) selectively performing an action in accordance with the action rule and in response to the results of the comparison.

Typically the action includes:
a) generating an alert notification; and,
b) providing the alert notification to a user by transferring the alert notification to a client device of the user via a communications network.

Typically the method includes generating a representation indicative of at least one of:
a) results of a comparison;
b) current domain scores;
c) reference domain scores;
d) current activity level scores;
e) reference activity level scores;
f) current activity level patterns;
g) reference activity level patterns; and,
h) the activity indicator.

Typically the method includes providing the representation to a client device via a communications network.

Typically the method includes determining a domain score using sensor data from a respective combination of sensors.

Typically the respective combination of sensors for each domain is determined based on at least one:
a) a sensor type; and,
b) a sensor location.

Typically the sensors include at least one of:
a) motion sensors;
b) power sensors that monitor operation of appliances;
c) temperature sensors;
d) humidity sensors;
e) accelerometers; and,
f) door sensors.

Typically the activity domain includes:
a) hygiene;
b) nutrition;
c) mobility;
d) transfer; and,
e) dressing/grooming.

Typically the method includes, for at least one domain:
a) identifying events using sensor data from the sensors; and,
b) determining the domain score using at least one of:
  i) a sum of a number of events during a time period; and,
  ii) a sum of a number of clusters of events during a time period.

Typically the method includes identifying events by comparing sensor data to a number of signatures, each signature being indicative of a respective event.

Typically the apparatus includes a hub provided in the living environment, the hub being adapted to communicate with each of the sensors and provided the sensor data to the at least one processing device, via a communications network.

Typically the apparatus includes a processing system including at least one processing device, the processing system communicating with one or more client devices via communications network, to at least one of:
a) provide alert notifications to the client devices; and,
b) allow the client devices to display a representation indicative of at least one of:
  i) results of a comparison;
  ii) current domain scores;
  iii) reference domain scores;
  iv) current activity level scores;
  v) reference activity level scores;
  vi) current activity level patterns;
  vii) reference activity level patterns; and,
  viii) the activity indicator.

It will be appreciated that the broad forms of the invention and their respective features can be used in conjunction and/or independently, and reference to separate broad forms of the invention is not intended to be limiting.

BRIEF DESCRIPTION OF THE DRAWINGS

An example of the present invention will now be described with reference to the accompanying drawings, in which:—

DETAILED DESCRIPTION OF THE PREFERRED EMBODIMENTS

Figure 1:
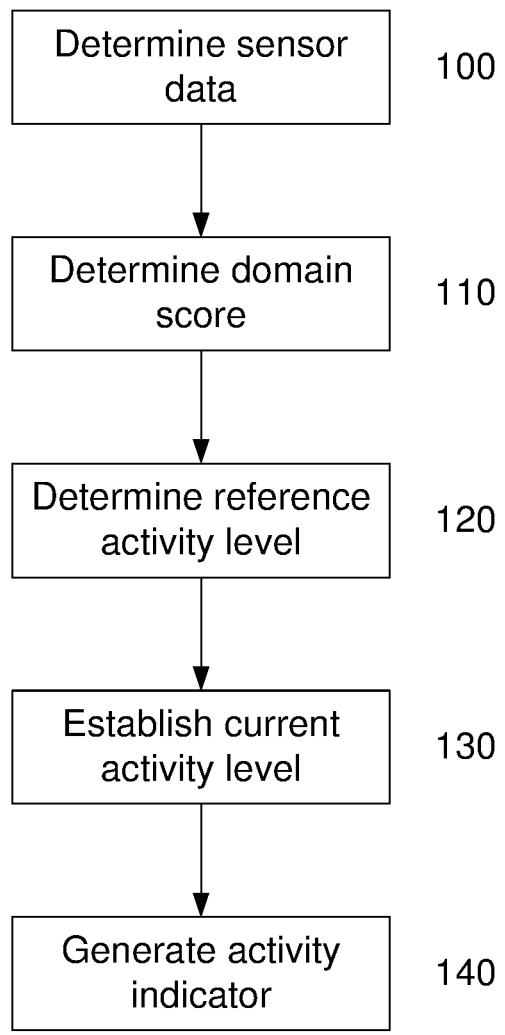
FIG. 1 is a flow chart of an example of a process for monitoring activity capabilities of an individual.

An example of a method for monitoring activity capabilities of a subject will now be described with reference to FIG. 1.

For the purpose of illustration, it is assumed that the process is performed at least in part using one or more electronic processing devices forming part of one or more processing systems, such as computer systems, servers, or the like, and which are optionally connected to one or more client devices, such as mobile phones, portable computers or the like, via a network architecture, as will be described in more detail below.

The processing device is in communication with a plurality of sensors, the sensors being positioned within a living environment of the subject, such as the subject's home. The sensors can be of any suitable form and are typically adapted to sense respective characteristics of the subject's activities, with a range of different sensors being provided allowing different characteristics of activities to be monitored. This can include, for example motion sensors that detect movement of the subject, power sensors that monitor operation of appliances, temperature sensors for detecting localised temperature changes, humidity sensors for detecting humidity in the environment, accelerometers for detecting movement of furniture or other items, contact sensors that detect door opening, or the like.

The sensors are typically mounted in the subject's living environment, so that an assessment can be made of the subject's activity capabilities, whilst the subject is performing day-to-day activities. By having the sensors mounted in the environment as opposed to, for example, being worn, the system is as unobtrusive as possible and avoids the need for any specific interaction by the subject. This is particularly important in the context of elderly or other impaired subjects that might struggle in order to effectively use worn sensors.

However, it will also be appreciated that data collected by other sensors, such as physiological sensors could also be used in addition to the use of sensors fixed within the environment. This can be used to supplement the information collected by the fixed sensors, for example allowing information regarding physiological parameters of the subject to be collected, although this is not essential and the system is adapted to be able to operate without such sensors, for example in the case that the subject forgets to wear the sensors.

In this example, at step 200 the processing device 110 determines sensor data indicative of sensor readings for each of the plurality of sensors, with the sensor data being at least partially indicative of activities performed by the subject. Thus, for example, motion sensors will be used to detect movement of the subject within their living environment whilst sensors such as accelerometers can be used to detect transitions from seated to standing positions, movement in bed or the like. Temperature sensors can be used to detect activities such as bathing or cooking whilst monitoring of appliances can be performed, for example, to detect food preparation activities or the like.

The sensor data can be received directly from the sensors. However, alternatively, the processing device could determine the sensor data by retrieving previously collected sensor data from a store, or receiving the sensor data from an intervening device, such as a hub, as will be described in more detail below.

At step 210, the processing device determines a domain score for each of a plurality of different activity domains. The domain score is indicative of a level of activity within the respective domain and is at least in part determined using sensor data from a respective combination of sensors.

Thus, different domains are defined corresponding to different types of activity. In general, these will include, but are not necessarily limited to domains including: meals, mobility, transfer, hygiene and dressing. These domains correspond to typical activities that a subject would be expected to perform as part of their day-to-day living. Thus, monitoring scores across each of these five domains allows an assessment to be made as to whether the subject is capable of caring for themselves, or whether additional assistance or interventions are needed.

It will be appreciated that the particular combination of sensor data used in order to determine the score will vary depending on the nature of the domain. For example, the meal domain will typically require monitoring of sensors that can detect meal preparation activities such as cooking, use of appliances, such as a kettle, oven or stove, or accessing food storage areas, such as cupboards, fridges, freezers, or the like. This is also typically constrained to a particular area, such as the kitchen.

In the case of hygiene, sensing is typically performed primarily in a bathroom or toilet, and could examine sensors relating to activation of sanitary fittings, as well as temperature and/or humidity settings, which can in turn be indicative of showering or the like. In the case of mobility sensing, this will typically be performed largely on the basis of movement sensors distributed throughout the living environment. Transfer, which examines the ability of a subject to change posture, can be performed on the basis of sensor data from accelerometers mounted within furniture, such as a bed or seat, as well as motion sensors, allowing an assessment to be made of the capability of a subject to stand, sit down, or otherwise change posture. Finally, in the case of dressing or grooming, this could include examining access to clothing storage, such as wardrobes, as well as use of related appliances, such as washing machines, irons, or the like.

It will be appreciated from this that the manner in which each domain score is calculated will vary depending on the nature of the domain and the type of sensors available, and specific examples will be described in more detail below.

At step 220, a reference activity level is established using reference domain scores measured during a reference time period. The reference activity level is used as a baseline and is measured in situ in order to establish a typical level of activity for the user, in their home environment. This is typically performed over an extended period of time, such as between one week and one month, as this allows an understanding of the typical degree of variation in the level of activity for the subject, and also enables the system to take into account differences in daily schedules of the subject, for example as the subject may have a set routine in which certain activities, such as washing or cleaning, or times absent from the home, are performed in a regular pattern. However, this is not essential, and in other examples, the reference time period could be based on shorter time periods, and could be based on a rolling time period, so that the reference time period is always taken to be the activity levels measured on a previous day.

During this reference time period, traditional monitoring of the user can also be performed in order to assess whether the reference activity level corresponds to an acceptable capability level, or whether this is deficient for some or all of the domains. This can be used to act as a reference point so that the determined domain scores can be correlated to an understood clinical assessment of activity capabilities. Thus, for example, a low mobility score for a user can be indicative of an inability to be mobile, or may result from the person being sedentary by nature. Accordingly, the assessment is made to establish a baseline that is typical for the subject, assuming a certain ability to perform activities and hence a certain level of ability to care for themselves.

At step 230 a current activity level is determined using current domain scores measured during a monitoring time period. Thus, after the baseline has been established, a similar process is performed in order to measure the current activity levels of the subject. This is performed repeatedly after the reference activity levels have been established allowing changes from the reference activity levels to be monitored. Monitoring of current activity levels can be performed on a regular basis, such as daily. In one example, the activity levels could be compared to comparable activity levels measured during the reference time period, based on a subject's schedule, so that for example, an activity level measured on a set day (such as a Wednesday), is compared to reference activity levels established for the same day (i.e.

Wednesdays) during the reference time period. Alternatively, as opposed to performing day-to-day comparisons, comparisons could be performed between respective types of day, such as to compare activity levels for weekdays with reference activity levels established for weekdays, and similarly comparing activity levels for weekends to reference activity levels for weekends.

At step 240, an activity indicator is generated at least partially in accordance with the current activity level and the reference activity level. The activity indicator is generated in such a way that it is at least partially indicative of differences between the current activity level and the reference activity level. Thus, this could simply be a visual display of the reference and current activity levels, allowing users to perform a visual side-by-side comparison of the reference and current activity levels. Alternatively however, some form of analysis could be performed, for example to compare the reference and current activity levels, and display results of the comparison. Further examples will be described in more detail below.

In any event this allows the activity level indicator to provide feedback on the activity capabilities of the subject, which in turn allows an assessment of a subject's activity capabilities to be performed. For example, this allows third party users, such as carriers, medical practitioners, family, or the like, to readily identify changes in activity capability and, in particular, degradation in activity capability, which can in turn be used to identify when intervention or assistance may be required.

In one example, this can be performed remotely, avoiding the need for ongoing onsite monitoring, thereby significantly reducing the burden on healthcare workers, whilst also allowing changes in capabilities to be identified without requiring input or feedback from the user, who may not be cognisant of a change, or unable or unwilling to communicate a change.

In any event, the above described system approach allows the activity capabilities of a subject to be monitored within the subject's own living environment, and with regard to the subject's day-to-day activities, as established during the reference time period. This ensures the assessment of activity capabilities are made in regard to activities that are actually of relevance to the subject in their current living circumstances. By way of example, if a subject lives in a single floor dwelling, the fact that the subject is unable to climb stairs may not be relevant to their ability to continue living at home, and hence this avoids the need to assess this capability.

Furthermore, monitoring is performed using sensors mounted within the living environment. This ensures that the activity capabilities of the subject can be quantified based on an objective assessment of the subject's capabilities performed in an automated manner, rather than relying on a subjective assessment of the subject's capabilities. Furthermore, this is achieved without the need for wearable sensors, which can be intrusive and may inadvertently be misused. This also allows a wider variety of sensors to be employed, allowing for greater scope in capability assessment.

A number of further features will now be described.

In one example, the method includes determining an activity level score by combining the domain scores. The reference activity level can then be determined using the activity level score measured during the reference time period, whilst the current activity level is determined using the activity level score measured during the monitoring time period. This allows a single numerical overall score to be calculated, providing a straightforward and easy to understand indicator of capability.

The activity level score can be determined using a simple sum of the domain scores, for example as a simple sum of the domain scores assessed from equally weighted domains, but alternatively could be calculated based on another mathematical function, such as a weighted sum, for example based on a degree of priority, relevance or severity of a condition, allowing this to take into account that different domains may have a different impact on a subject's ability to manage without assistance or intervention. This can be used to prioritise particular domains over others when an overall score is calculated, for example to take into account domains of particular relevance to the subject. Thus, for a subject with dietary complications, a meal activity domain might be given a higher weighting and hence higher priority than other domains, such as transfer or movement. It will be appreciated from this that the weighting used may depend on circumstances relevant to the subject, such as one or more conditions from which the subject suffers.

Whilst a combination may be used to provide an overall score, however, this is not essential and other assessments could be performed. For example, the method could include determining an activity pattern indicative of relative values of domain scores, determining the reference activity level using the activity pattern measured during the reference time period and then determining a current activity level using a current activity pattern measured during the monitoring time period. Thus, this will examine if there is a change in the relative activity in different domains, highlighting for example, that whilst a subject is still mobile, they may have lost appetite. The activity pattern may also be used as a signature to identify certain events. For example, if a subject's mobility suddenly drops dramatically, this could be indicative of a fall or other similar event.

As a further alternative, assessment could be performed based on examination of the domain scores for each of the domains respectively, performing a comparison of each current domain score to a corresponding reference domain score.

In one example, the method includes comparing a current activity level to the reference activity level and then generating the activity indicator at least partially in accordance with results of the comparison. Thus, this allows changes from the reference activity level to be easily identified. The comparison can be performed in any one of a number of ways which could include any one or more of comparing each current domain score to an equivalent reference domain score, comparing each current domain score to a respective reference range derived from an equivalent reference domain score, comparing a current activity level score to a reference activity level score, comparing a current activity level score to a respective reference range derived from a reference activity level score and a current activity pattern to a reference activity pattern.

Additionally and/or alternatively, a current activity level can be compared to a reference activity level measured during a corresponding time period, such as the same day from an earlier week. Thus, for example, if the reference activity levels show patterns or trends, such as particular levels of activity on particular days of the week, as may occur for a subject's day to day routine, then the current activity level measured for a particular day could be compared to reference activity levels measured on the same day during the reference time period, thereby allowing the subject's particular routine to be taken into account.

Thus, it will be appreciated from this that comparisons could be performed between overall activity scores and/or subject domain scores. Additionally, whilst direct comparison could be performed, alternatively comparison could be to ranges established using the reference activity level or reference domain scores. Thus as opposed to comparing measured domain scores to absolute domain score values, the comparison could be to a value range based on the measured reference domain scores, for example based on a standard deviation of reference domain scores over a defined time period. The reference ranges could be used to reflect day to day differences in activity levels, as well as typical variations that would be expected for the subject, optionally taking into account conditions suffered by the subject. Thus the range could be determined from the reference activity level scores or domain scores, for example looking at a variation of activity level or domain scores for a particular domain, over the reference time period. Thus, this can provide a longitudinal analysis in which data gathered over a time period is used to predict an individual's own profile. Alternatively, this might be established based on a sample population, of typically similar individuals, and could also be specific to a particular condition suffered by the subject. For example, this can be used to define a restricted range in the event that activities in a particular domain are critical, such as ensuring adherence to diet for a diabetic, or more lax in the event that the domain is of less importance to the subject's wellbeing. Accordingly, in one example, the method includes determining a condition suffered by the subject and determining a combination of domains, domain scores, or domain score ranges, at least partially in accordance with the condition, thereby allowing domains of most relevance to the condition to be given priority in the assessment.

Having performed the comparison, the method can further include determining an action rule and selectively performing an action in accordance with the action rule and in response to the results of the comparison. In this regard, action rules can be determine for each subject being monitored, with the action rule defining one or more actions that might need to be performed depending on the results of the comparison.

Whilst any form of action could be performed, in one example, the method includes selectively generating an alert notification in response to results of the comparison and providing the alert notification to a user, such as a carrier, medical practitioner, family member, or the like. The alert notification can be used to alert the user that an event has occurred, such as the subject has failed to eat or move in a defined time period, allowing appropriate action to be taken, such as allowing the user to follow up and be provided with appropriate care or intervention.

As part of this process, the method can include identifying at least one user depending on the results of the comparison. This allows different users to be notified depending on the results of the comparison. For example, if the comparison indicates that mobility has reduced but not stopped completely, a carrier could be alerted. However, if mobility has ceased completely, then emergency services could be notified, allowing appropriate emergency intervention to be provided.

Once the relevant users have been identified, the method typically includes providing the alert notification to at least one user by transferring the alert notification to a client device of the user via a communications network. This allows the user to be alerted automatically, using a device such as a smart phone, mobile phone or the like, allowing them to take appropriate action in a rapid manner. The alert could simply be a notification that an issue has been detected, but could also provide additional information, such as a representation indicative of the activity indicator, allowing the relevant user to make an assessment of what action, if any, should be taken.

A representation of the activity indicator and/or other information could also be generated and provided to users for viewing at other times, such as on demand. This could be achieved in any appropriate manner, such as by providing the representation to a client device via a communications network in response to a request. This could be provided in any suitable manner, such as through a user interface displayed by an application, as part of a webpage, or the like. The representation could include a range of different information, including but not limited to results of a comparison, current domain scores, reference domain scores, current activity level scores, reference activity level scores, current activity level patterns, reference activity level patterns and the activity indicator.

As previously mentioned, the domain score can be determined using sensor data from a respective combination of sensors. This allows different combinations of sensors to be used in establishing different domain scores, as will be described in more detail below.

The sensors are typically mounted in an environment used by the subject, and in particular are typically provided throughout a living environment of the subject, allowing monitoring to be performed for all of the subject's day-to-day activities. Determining a domain score can therefore be performed based at least in part on a location of the sensors. For example, this can be performed by monitoring sensors provided within a respective room, so hygiene may be largely based on sensors located within a bathroom or toilet facility, whereas meal domain scores will typically be based on sensors provided in a kitchen and/or dining room.

Additionally, the sensors used will also typically depend on a sensor type. For example, motion sensors could be used to determine mobility, whilst operation of appliances or the like, can be used to assess activities such as meal preparation. Typically the sensors include, but are not limited to motion sensors, power sensors that monitor operation of kitchen appliances, temperature sensors, humidity sensors, accelerometers and door sensors, such as reed switches mounted to the door.

In one example, the process of monitoring the sensors includes identifying events using sensor data from the sensors and determining the domain score using either a sum of a number of events during a time period or a sum of a number of clusters of events during a time period. The events could be identified in any suitable manner, and this could include comparing sensor data to a number of signatures, each signature being indicative of a respective event. Thus the signature could be indicative of a particular sensor reading or pattern of sensor readings, and could include readings from multiple sensors simultaneously, allowing different events to be more accurately identified. Thus, this allows individual events to be easily identified, with the events being viewed collectively in order to allow a score for each domain to be established.

Figure 2:
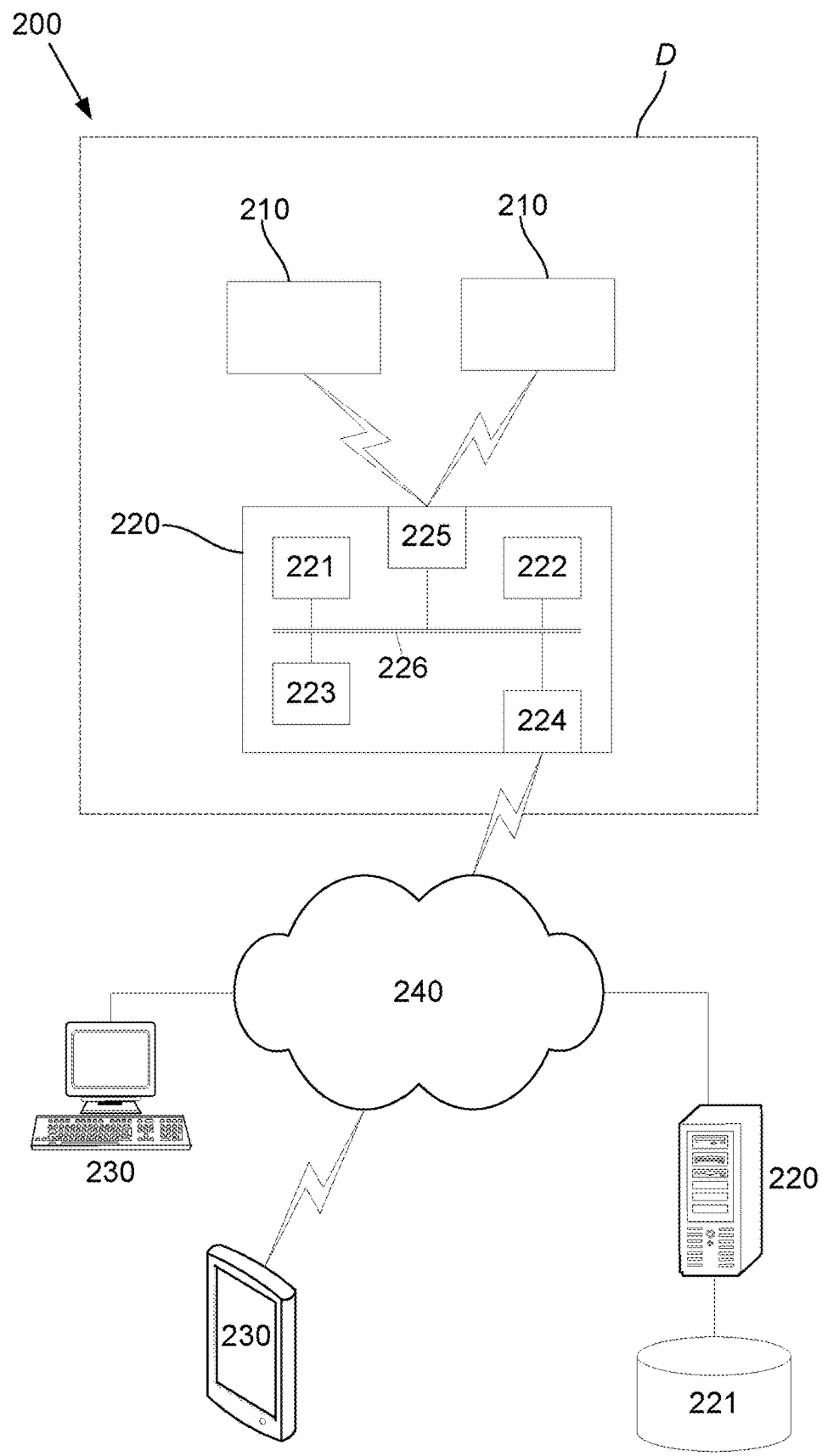
FIG. 2 is a schematic diagram of a second example of apparatus for monitoring activity capabilities of an individual.

An example of a system for use in activity monitoring will now be described with reference to FIG. 2.

In this example, the system 200 includes a number of sensors 210 each of which is coupled to a hub 220, which in turn is in communication with one or more client devices 230 and/or a processing system, such as a server 250, via one or more communications networks 240.

In this example, the sensors 210 and hub 220 are provided in a subject's dwelling D, which could be a house, apartment, or the like. The sensors 210 are typically mounted throughout the dwelling, at appropriate locations, and may be coupled to furniture, fixtures or fittings as required. The sensors 210 are therefore typically wirelessly coupled to the hub 220 using a suitable communications technique, such as Bluetooth, WiFi, or the like, allowing for ease of installation, although this is not essential and wired communication could be used.

In one example, the hub 220 includes a hub processor 221, a hub memory 222, an optional hub input/output device 223, such as a keyboard and display or touchscreen, an external interface 224 and a sensor interface 225, interconnected via a bus 226. The sensor interface 225 is adapted to wirelessly communicate with the sensors 210, whilst the client device interface 224 is adapted to allow communications with a client device 230 either directly, or via an intermediate communications network 240 as shown. Although a single external interface is shown, this is for the purpose of example only, and in practice multiple interfaces using various methods (e.g. Ethernet, serial, USB, wireless or the like) may be provided. Similarly, the external interface 224 and sensor interface 225 could in fact be provided by a single interface, such as a wireless network interface, and reference to separate interfaces is not intended to be limiting but rather is for the purpose of illustration.

In use, the hub processor 221 executes instructions in the form of applications software stored in the memory 222 to enable communication with the sensors, allowing sensor data to be received and provided to the server 240. As part of this, some processing may be performed, for example to sample and/or interpret signals from the sensors and generate the sensor data. The applications software may include one or more software modules, and may be executed in a suitable execution environment, such as an operating system environment, or the like.

Accordingly, it will be appreciated that the hub 220 may be formed from any suitable processing system, such as a suitably programmed computer system, although this is not essential and the processing system could be any electronic processing device such as a microprocessor, microchip processor, logic gate configuration, firmware optionally associated with implementing logic such as an FPGA (Field Programmable Gate Array), or any other electronic device, system or arrangement. The hub could be in the form of a suitably programmed computer system, server, or other processing system, or could include a communications device, such as a mobile phone, smart phone, or the like.

In use, actions performed by the hub 220 are performed by the hub processor 221 in accordance with instructions stored as applications software in the memory 222 and/or input commands received from a user via the I/O device 223, or commands received from the client device 230 or server 250, as will be described in more detail below.

The communications network 240 can be of any appropriate form, such as the Internet and/or a number of local area networks (LANs) and provides onward connectivity to one or more client devices 230 and the server 250, which is in turn coupled to a database 251. It will be appreciated that this configuration is for the purpose of example only, and in practice the hub 220, client devices 230 and servers 250 can communicate via any appropriate mechanism, such as via wired or wireless connections, including, but not limited to mobile networks, private networks, such as an 802.11 networks, the Internet, LANs, WANs, or the like, as well as via direct or point-to-point connections, such as Bluetooth, or the like.

In one example, the server 250 is adapted to interpret sensor data and provide access to the resulting activity indicators and other information, as well as generating representations and/or alerts as required, with these being provided to the client devices 230 as required. Whilst the server 250 is a shown as a single entity, it will be appreciated that the server 250 can be distributed over a number of geographically separate locations, for example by using processing systems and/or databases 251 that are provided as part of a cloud based environment. However, the above described arrangement is not essential and other suitable configurations could be used.

Figure 3:
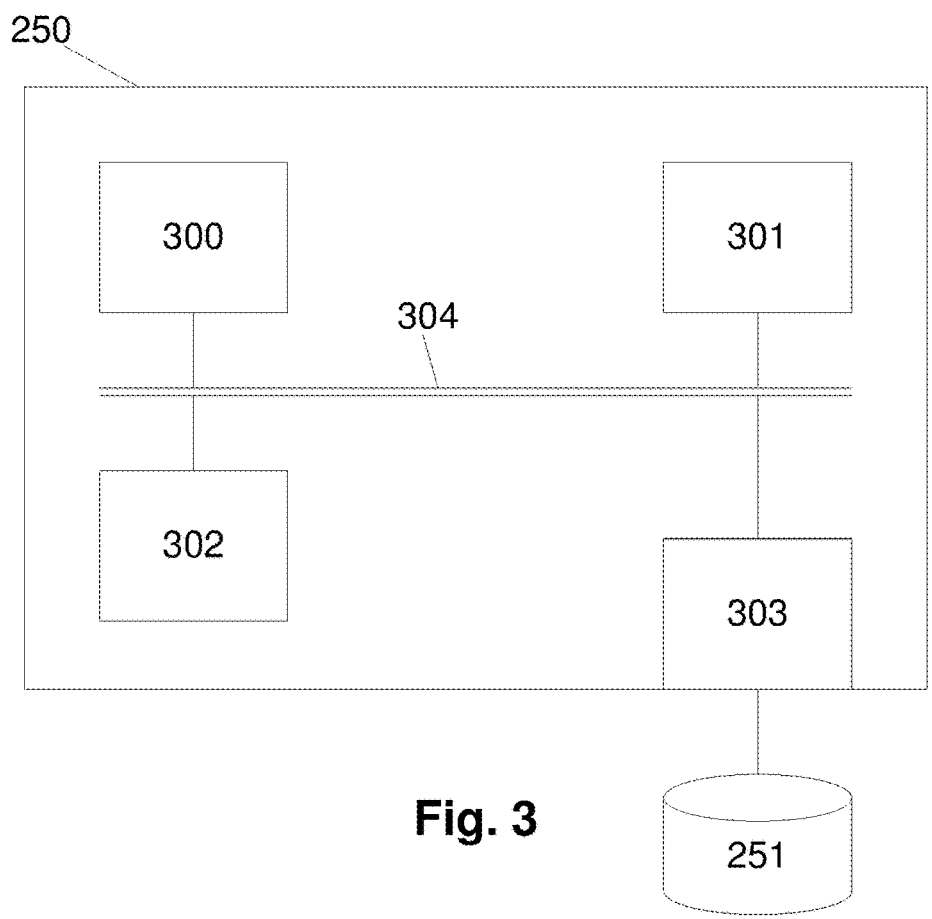
FIG. 3 is a schematic diagram of an example of a base station processing system.

An example of a suitable server 250 is shown in FIG. 3. In this example, the server includes at least one microprocessor 300, a memory 301, an optional input/output device 302, such as a keyboard and/or display, and an external interface 303, interconnected via a bus 304 as shown. In this example the external interface 303 can be utilised for connecting the server 250 to peripheral devices, such as the communications networks 240, databases 211, other storage devices, or the like. Although a single external interface 303 is shown, this is for the purpose of example only, and in practice multiple interfaces using various methods (e.g. Ethernet, serial, USB, wireless or the like) may be provided.

In use, the microprocessor 300 executes instructions in the form of applications software stored in the memory 301 to allow the required processes to be performed, including communicating with the client devices 230, generating webpages for example including representations of the activity indicator and/or other information. The applications software may include one or more software modules, and may be executed in a suitable execution environment, such as an operating system environment, or the like.

Accordingly, it will be appreciated that the server 250 may be formed from any suitable processing system, such as a suitably programmed client device, PC, web server, network server, or the like. In one particular example, the server 250 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement.

Figure 4:
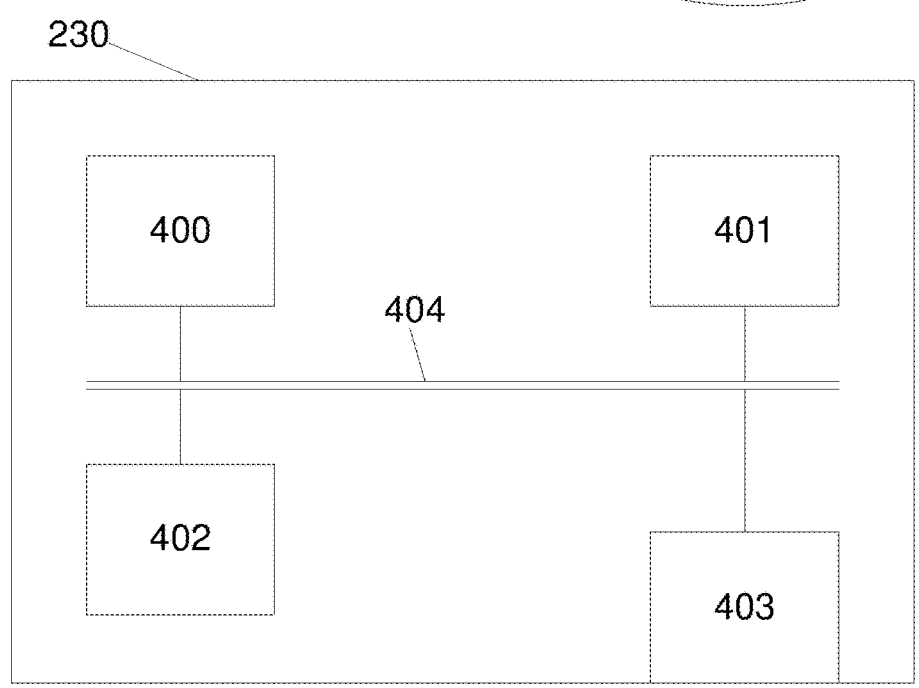
FIG. 4 is a schematic diagram of an example of a client device.

As shown in FIG. 4, in one example, the client device 230 includes at least one microprocessor 400, a memory 401, an input/output device 402, such as a keyboard and/or display, and an external interface 403, interconnected via a bus 404 as shown. In this example the external interface 403 can be utilised for connecting the client device 230 to peripheral devices, such as the communications networks 240, databases, other storage devices, or the like. Although a single external interface 403 is shown, this is for the purpose of example only, and in practice multiple interfaces using various methods (e.g. Ethernet, serial, USB, wireless or the like) may be provided.

In use, the microprocessor 400 executes instructions in the form of applications software stored in the memory 401 to allow communication with the server 250, for example to allow for representations of the activity indicator to be viewed, and to receive alerts, or the like.

Accordingly, it will be appreciated that the client devices 230 may be formed from any suitable processing system, such as a suitably programmed PC, Internet terminal, laptop, or hand-held PC, and in one preferred example is either a tablet, or smart phone, or the like. Thus, in one example, the client device 230 is a standard processing system such as an Intel Architecture based processing system, which executes software applications stored on non-volatile (e.g., hard disk) storage, although this is not essential. However, it will also be understood that the client devices 230 can be any electronic processing device such as a microprocessor, microchip processor, logic gate configuration, firmware optionally associated with implementing logic such as an FPGA (Field Programmable Gate Array), or any other electronic device, system or arrangement.

Examples of the operation of the system for monitoring activity capabilities of a subject will now be described in further detail. For the purpose of these examples it will also be assumed that users interact with the system via a GUI (Graphical User Interface), or the like presented on the client device 230, which may be generated by a local application, or hosted by the server 250 and displayed via a suitable application, such as a browser or the like, executed by the client device 230. Actions performed by the client device 230 are typically performed by the processor 400 in accordance with instructions stored as applications software in the memory 401 and/or input commands received from a user via the I/O device 402. Actions performed by the hub 220 are performed by the processor 221 in accordance with instructions stored as applications software in the memory 222 and/or input commands received from a user via the I/O device 223, or commands received from the client device 230 or server 250. Similarly, actions performed by the server 250 are performed by the processor 300 in accordance with instructions stored as applications software in the memory 301 and/or input commands received from a user via the I/O device 302, or commands received from the client device 230.

However, it will be appreciated that the above described configuration assumed for the purpose of the following examples is not essential, and numerous other configurations may be used. It will also be appreciated that the partitioning of functionality between the hub 220, client devices 230, and servers 250 may vary, depending on the particular implementation.

For example, in the current configuration, the purpose of the hub 220 is to allow multiple subject sensors to be monitored, with sensor data being passed onto the server 250 for subsequent analysis. It will be appreciated from this that the use of the hub, whilst convenient is not essential, and similar functionality could be achieved by having the sensors 210 communicate directly with the server 250, for example via an Internet of Things (IoT) type configuration, or by having functionality performed by the server 250 implemented locally by the hub or another suitable processing system. However, the use of hub 220 and server 250 is particularly advantageous as it offloads at least some coordination of the sensor data to a local device, whilst allowing monitoring to be performed centrally. This allows for greater oversight by users and also allows the analysis performed to be modified dynamically as required. Furthermore, it will be appreciated that whilst two sensors are shown, this is for the purpose of illustration only, and in practice a larger number of sensors 210 would typically be provided.

An example of operation of the system described above will now be described with reference to FIGS. 5 and 6, which show the process of determining an activity level indicator, and determining monitoring activity capabilities respectively.

Figure 5:
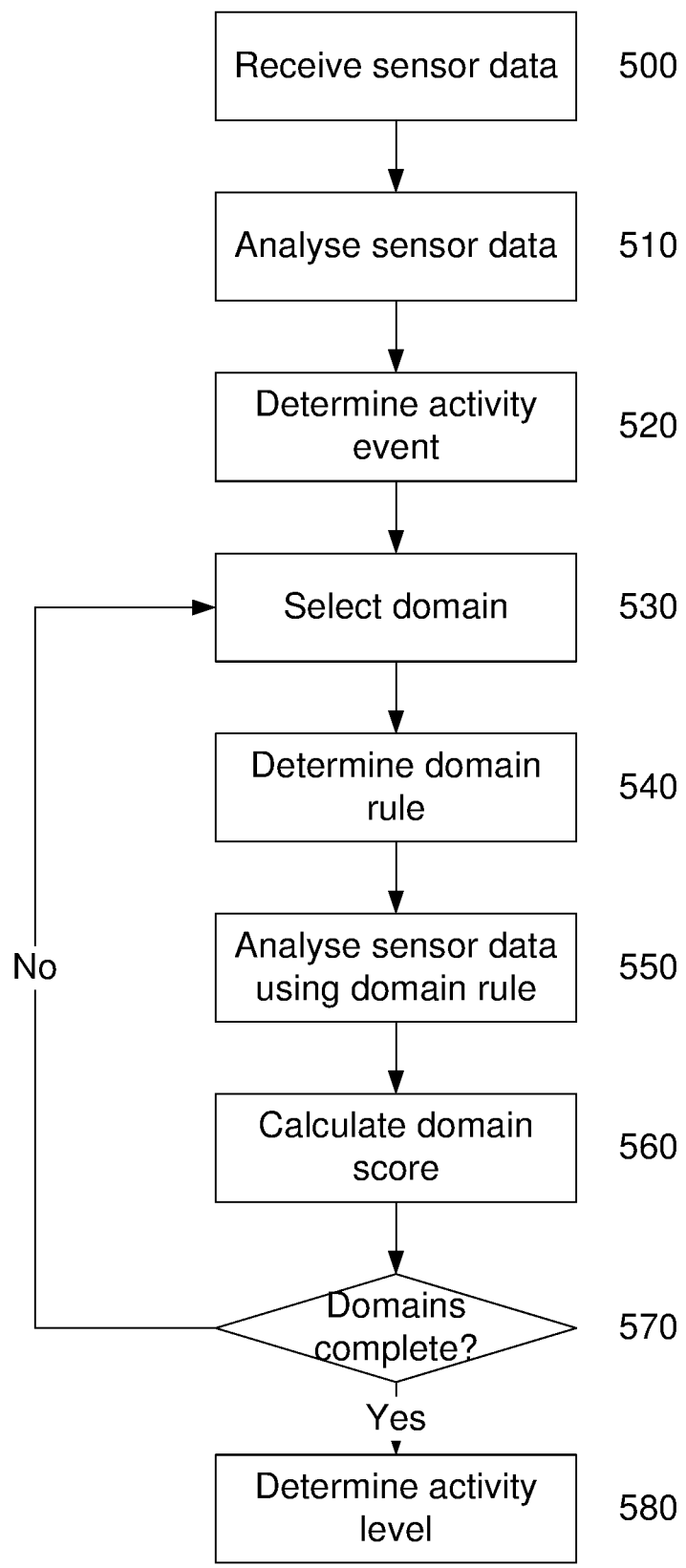
FIG. 5 is a flow chart of an example of a method for monitoring activity capabilities of an individual.

In the example of FIG. 5, at step 500 an indication of sensor readings is received by the server 250 from the hub 220. This could be performed continuously, although more typically the hub 220 will monitor signals from the sensors and then cache these locally, generating and transferring sensor data to the server 250 on a periodic basis, such as every hour, twice a day, or the like, depending on monitoring requirements.

At step 510, sensor data is analysed, with this being used to identify individual activity events at step 520. The manner in which this is performed will vary depending on the nature of the sensor and relevant events. For example, this could include detecting opening of a door, use of an appliance, movement between rooms or the like, and example of this will be described in more detail below.

At step 520, a next domain is selected with this being used to determine a corresponding domain rule at step 530. The domain rule specifies how a domain score is calculated from the sensor data, taking into account the available sensors and their respective locations.

In this regard, it will be appreciated that each subject's residence is typically unique, and will include a respective layout of rooms and furniture. For this reason alone, the particular sensor configuration used in each dwelling will also be unique, depending for example on factors such as locations in which sensors can be mounted. Additionally however, different sensor configurations could be defined for different subjects, depending on their particular functional capabilities, so for example, for a subject with known mobility restrictions, it may be desirable to include additional movement sensors, allowing mobility to be tracked with a higher degree of accuracy. Accordingly, when the dwelling is initially configured with sensors, it is typically to define a custom domain rule for each domain, the domain rule defining the particular combination of sensors that should be used in order to generate a respective score.

Additionally, the manner in which the score are generated will vary depending on the nature of the sensors and the particular contribution to activity events relating to the domain. Typically this involves analysing the sensor data for each type of sensor, and using this to identify events, as described at steps 510 and 520 above. Thus, this will typically include identifying events such as a number of times the subject has changed posture, how many steps have been walked, how many times appliances have been used or the like. Identification of events is typically performed by analysing one or combined sensor readings to detect the gradation of the cluster of activities for the particular patterns of readings, with the number of resulting events then being tallied to generate the score. The domain rule will therefore also specify which criteria should be used to identify subject events, and then how these should be tallied or otherwise interpreted in order to generate a domain score.

In any event, at step 560 the sensor data and domain rule are used to determine a domain score, and specific examples of this process will be described in more detail below.

At step 570, it is determined if all domains are complete, and if not the process returns to step 530 to select a next domain. Otherwise, at step 580, the domain scores are used to determine an activity level, also known as an activities of daily living level, which could be in the form of a single combined score, a pattern or relative scores, or the like, depending on the preferred implementation.

Figure 6A:
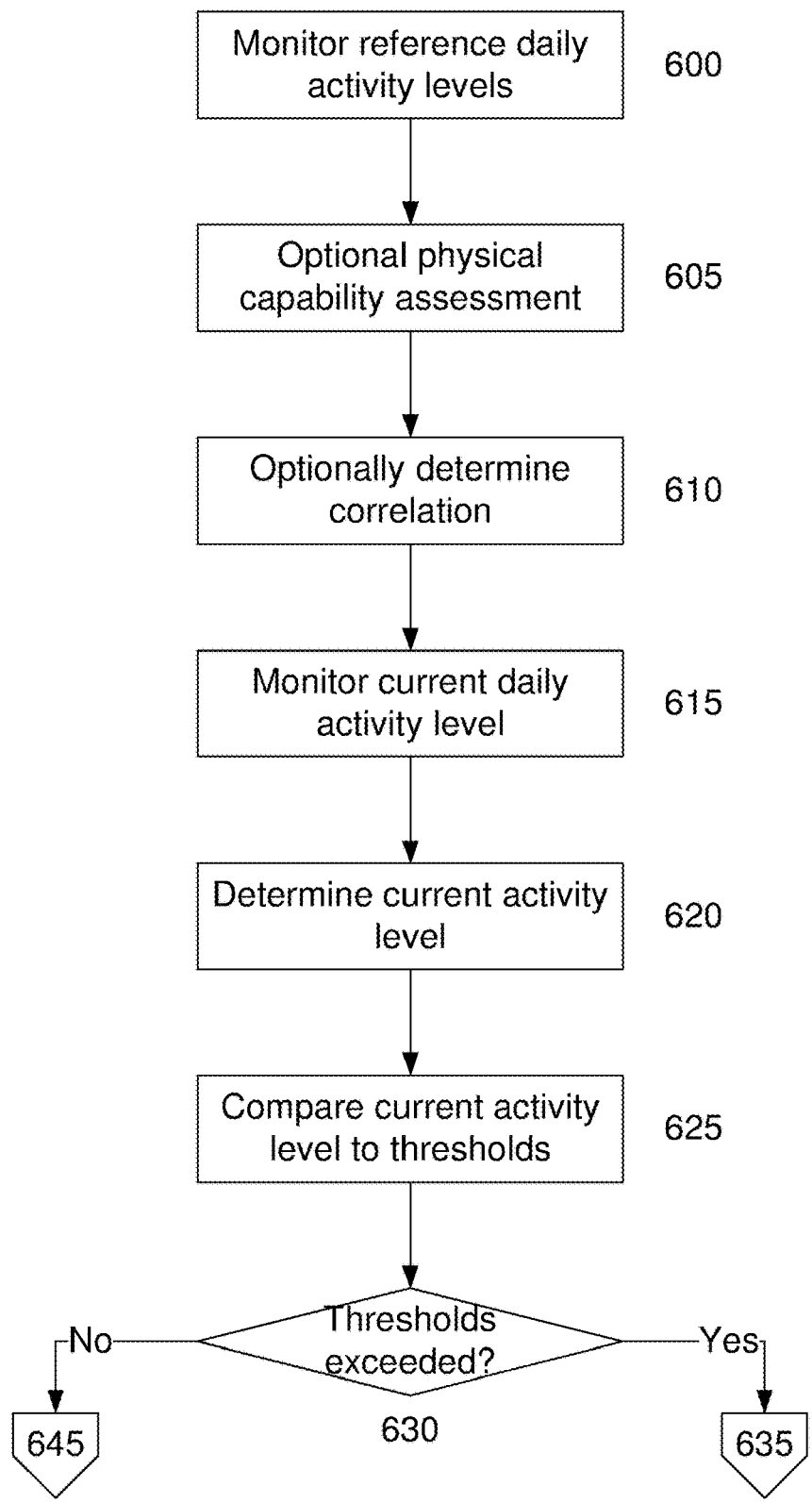
FIGS. 6A and 6B are a flow chart of a method of monitoring activity capabilities of an individual.
Figure 6B:
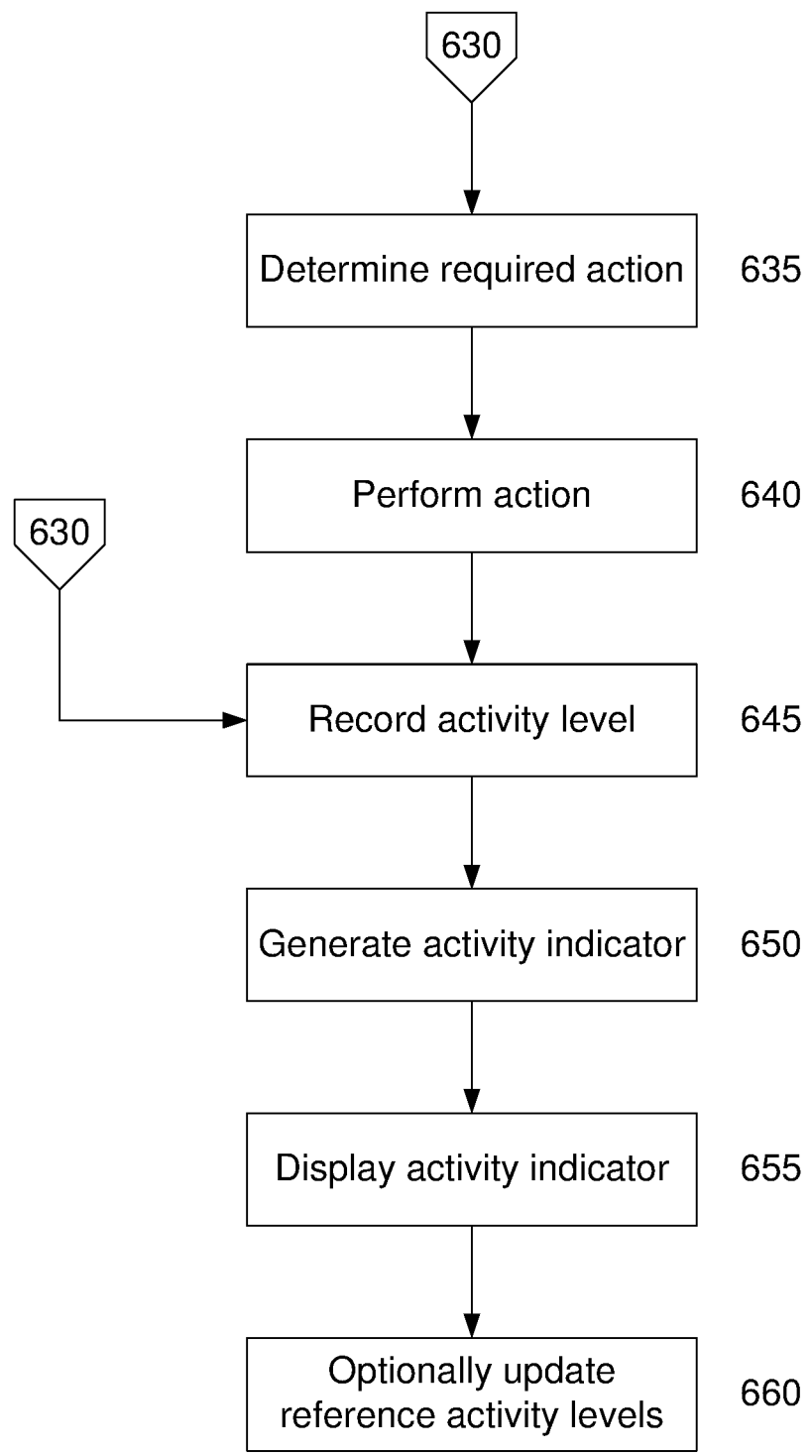

The process for ongoing monitoring of a subject's activity levels will now be described with reference to FIGS. 6A and 6B.

In this example, at step 600 a reference activity level is determined by having the server 250 determine domain scores during a reference time period. Thus, it will be appreciated that this involves performing the process of FIG. 5 during a reference time period. The reference time period can be of any appropriate duration, but typically extends over at least one week, and more typically a month, with individual daily scores being generated allowing variations in activity levels of the subject to be determined, and in particular allowing an assessment to be made of any patterns, such as any correlation of activity levels with particular days of the week.

During this process, a physical activity capability assessment can be performed at step 605. This can be performed in any suitable manner, such as through third party assessment by a clinician or other carrier, or through self-assessment by the subject or a combination of these approaches. This allows a correlation between a daily activity level and functional capabilities to be established at step 610, for example to determine if a particular domain score corresponds to a particular condition, circumstance, episode, or the like. As part of this initial monitoring process, the subject may be assessed to decide in what circumstances actions might need to be performed, allowing an action rule to be created defining when and what actions are required, as will be described in more detail below.

At step 615, the server 250 monitors a current activity level, for example by determining domain scores in a current time period using the process outlined above with respect to FIG. 5.

The current activity level and, in particular the subject domain scores, are then compared to respective thresholds at step 620. The thresholds are typically in the form of a threshold range, corresponding to an expected range of domain scores, as determined using the reference domain scores. The ranges could be based solely on the absolute domain scores, with a fixed range either side of the score. More typically however, the ranges are based on variations in the domain score during the reference time period, so if a high degree of variation is typical for a subject, then a correspondingly large range would be considered as normal. The thresholds could also be based on the particular time period being measured, for example to compare to a corresponding reference time period, so for example, if the current day is a weekday, then the current activity levels could be compared to thresholds established from reference activity levels also measured on weekdays. However, more specific time periods could be used, for example to take into account routine activities. For example, if the individual fails to attend a regular appointment, this could be indicative of an issue, which in turn could be used to trigger an alarm or the like. Additionally and/or alternatively, the thresholds could be based on conditions suffered by the subject, for example to define a narrower threshold range for a domain that is of particular importance to the subject, and their ability to perform day to day activities.

At step 625 it is determined if the thresholds are exceeded, the process proceeds to step 630 to determine if any action needs to be taken. In this regard, the need to take action will typically differ for each subject, and may therefore be uniquely defined depending on the requirements of the subject. Accordingly, the server 250 can access an action rule for the subject and determine from this what action is required, if any.

In this regard, whether action is required could depend on a range of different factors, such as the particular threshold(s) that are exceeded, the degree by which these are exceeded, whether this is the first time the threshold is exceeded, a time since this or other thresholds were last exceeded or the like. For example, the first time a threshold is exceeded may not warrant further action, but if the same threshold is exceeded two days running, or three times within a week, then action might be required.

The nature of the actions that can be performed will vary depending on the preferred implementation, but typically includes alerting one or more users of the system, including but not limited to care givers, relatives, assigned medical personnel, emergency services, or the like. It will also be appreciated that the user could be selected based on the results of the comparison, as defined by the action rule. So for example, the first time a threshold is exceeded, a relative or carrier might be informed, whilst the second time, medical services could be informed.

Thus, it will be appreciated that action rules can be established determining what actions are required depending on the results of the comparison, and also on other factors, such as the results of previous comparisons, and/or actions taken. Having established what action is required, this is then typically performed at step 635. For example, if one or more users are to be alerted, the server 250 generates an alert notification, such as a text message, email, or the like, and then transfers this to a relevant client device 230 via the communications network 240 at step 640.

At step 645, the server 250 stores an indication of the activity level, and optionally additional information, such as the subject domains scores and details of any actions performed.

At step 650, the server 250 generates an activity level indication, typically by generating a graphical representation of the activity level and/or results of the comparison, with this being displayed to users on demand, for example as part of a dashboard displayed on a webpage, application, or the like at step 655. This allows users to access and view activity levels at any time, allowing ongoing monitoring of current and historical activity levels to be performed, which in turn can form part of an ongoing functional capability assessment program.

It will be appreciated that the above described process would typically be performed continuously on an ongoing process. As part of this procedure, at step 660, reference activity levels may be optionally updated taking into account current activity levels, for example, to reflect ongoing progression of a condition and hence user's activity capabilities. Thus, if a subject is undergoing rehabilitation and their activity capabilities gradually improve, then it might be desirable to update the reference activity levels to reflect these changes. Alternatively if an individual undergoes a slight but significant decline in the behavioural patterns that is related to psychological decline e.g. mild cognitive impairment, then the comparison will be made against new update reference ADL profile or score to either put a new intervention to manage or improve the impairment.

A specific example process will now be described in more detail.

In this example, the activity monitoring system aggregates information from wireless sensors placed in a person's living environment to gather/infer ambient, physical, physiological, and psychological conditions of that person to establish a profile of the subject's functional and health status to enable support from informal or formal carriers. The functional status uses the activities daily living framework used in clinical settings.

Figure 7:
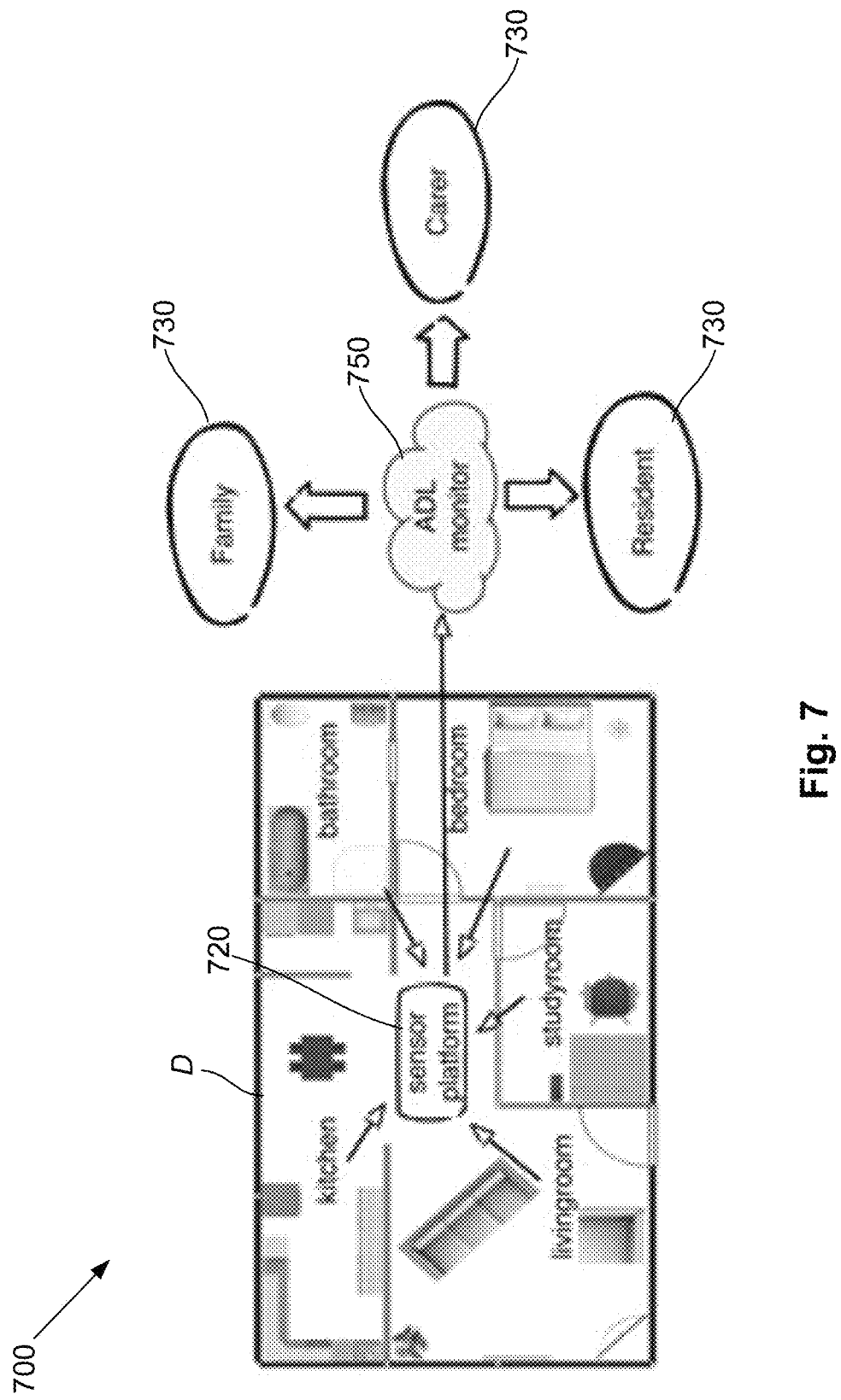
FIG. 7 is a schematic diagram showing a typical sensor arrangement for monitoring activity capabilities of an individual.

An example configuration is shown in FIG. 7, in which sensors are provided in the dwelling D, thereby detecting home activity, with sensor data being collated by a hub in the form of a sensor platform 720, with sensor data being passed to a cloud based monitor 750, which collects, processes, and presents the results to users, such as family, carriers and residents, via respective client devices 730.

The main processes involved can be categorized as:

Data Collection: where continuous raw data from non-intrusive sensors in a home environment, and physiological data such as blood pressure, body temperature from wireless clinical measurement devices are gathered wirelessly by a server;

Data Analysis: data collected are transmitted to a cloud to extract defined daily activities, namely meal (preparing and attending to a meal), transfer (postural changes e.g. waking from bed), dressing/grooming (ability to clothe and any appearance related task), hygiene (attending to washing, shower, etc.), and mobility (ability move around within home and/or outside), from raw sensor data through human behavior pattern analyses algorithms; evaluating extracted ADL patterns through ADL scores to understand daily health status and functional status of an independent living, at home (such as an older person);

Presentation: The data is then presented in numerical and graphical presentation relevant to the end-user's interpretation, including but not limited to:

Self-monitoring/management (for resident at home being supported), family members, friends or neighbours engaged in the support for the wellbeing of the person being supported (e.g. An elderly parent). This would be provided via a lifestyle tablet PC or other similar client device.

Family members or carriers to gain access to wellbeing parameters that provide an insight into the lives of their elderly parent living alone through the family portal by a web browser.

Healthcare practitioner or clinical services to correspond any significant health changes to in correspondence to daily functional status.

The key domains of activities of daily living (ADL) comprise mobility, transfer, hygiene, dressing, and meal preparation. While such domains are assessed typically in a clinical setting by a clinical personnel, is this approach is not only limited by the subjectivity of the ADL assessment but also by the unreflective, artificial environment of and tasks on which the subject is assessed. However, by using the above described approach, sensor data can be used to generate quantified indicators, removing the subjectivity, and ensuring a more reliable and consistent measure is established.

Figure 8:
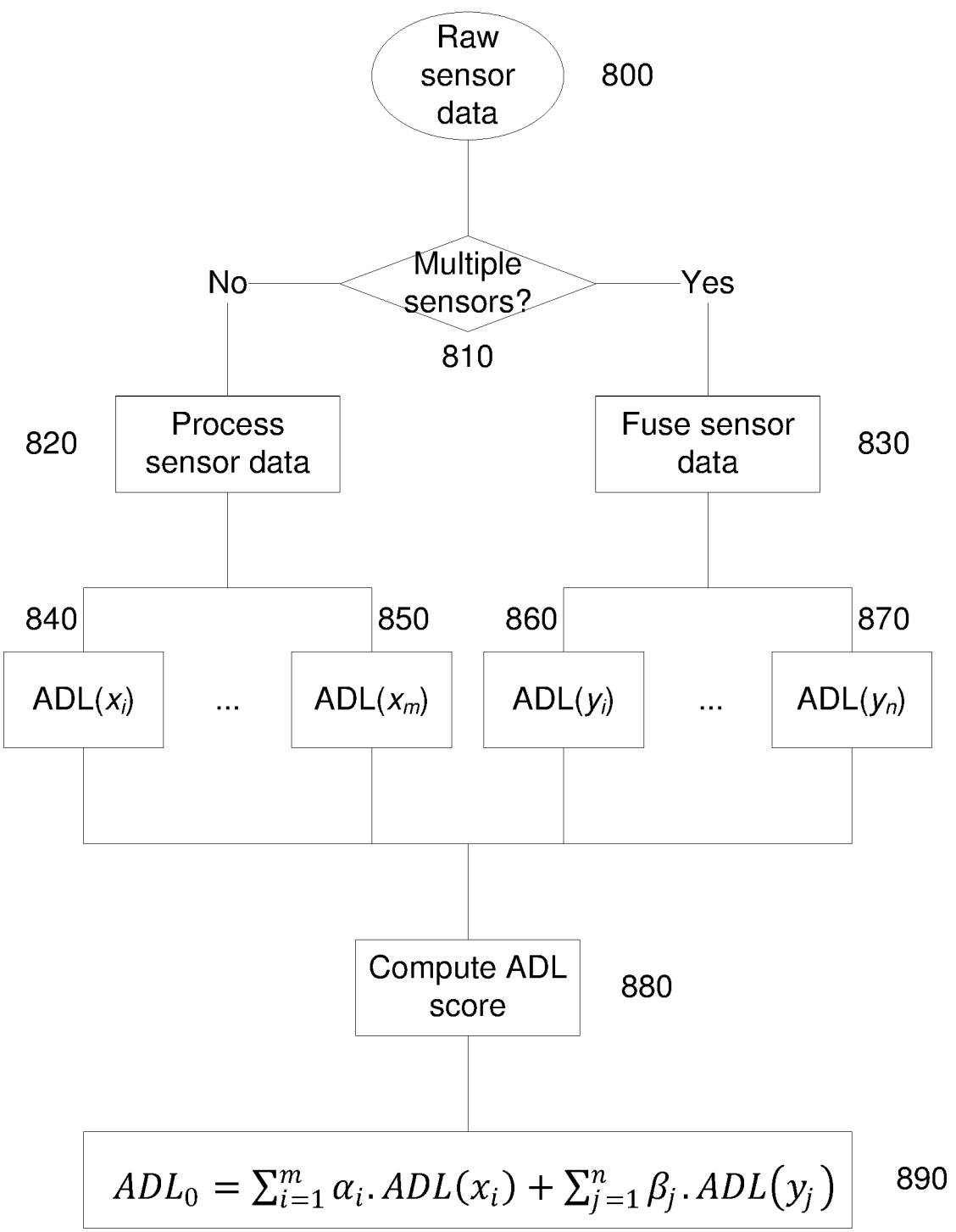
FIG. 8 is a flow chart of an example of a technique for calculating domain scores.

An example of the process for extracting an ADL score is shown in FIG. 8.

In this example, raw sensor data is obtained at 800, from sensors placed at somewhat 'invisible' and non-intrusive position to residents in their home environment are communicated wirelessly via low-powered protocol (e.g. via ZigBee or Bluetooth or WiFi) to a local sensor hub. Depending on the ADL domain of interest, activities are gathered from either one or multiple sensors, whether specific to a location or multiple interactions of home appliances and fittings. For example, to identify a meal preparation in modern homes, a combination of power outlet sensors to detect kitchen electrical appliances and/or stove, contact sensor can detect use of refrigerator and pantry cupboards to access food items, etc. would determine a meal activity.

Accordingly, it is determined if there are multiple sensors at 810. If not, the sensor data is processed at 820 to generate scores for each domain $ADL(x_i) \ldots ADL(x_m)$ at 840 ... 850. If there are multiple sensors, the sensor data is fused at 830 before scores are generated each domain $ADL(y_i) \ldots ADL(y_n)$ at 860 ... 870. This is then used to compute an ADL score at 880, using equation (1):

$$ADL_0 = \Sigma_{i=1}^{m} \alpha_i \cdot ADL(x_i) + \Sigma_{j=1}^{n} \beta_j \cdot ADL(y_j) \qquad (1)$$

Examples of the types of raw sensors relating to the placement corresponding to home activity are described below in Table 1.

TABLE 1

| Sensor Type | Data Gathered | Place of installation |
| --- | --- | --- |
| Motion sensor | Incidents of motion within operating range install | Ceiling in all rooms |
| Power sensor | Current draw of various appliances and devices | Wall power outlets |
| Temperature/ Humidity sensor | Temperature and humidity readings with a frequency dependent on sensor and/or application | Bathroom and kitchen in the house |
| Accelerometer | Movements in the bed/chair | Attached to the bottom of the bed/chair |
| Circuit meter | Stove usage monitoring | Attached to the electrical switchboard panel |
| Reed switch | Doors open/close | Bedroom wardrobe, kitchen pantry door and freezer door |

From a somewhat comprehensive deployment of simple environmental wireless sensors instrumented in a 2 bedroom home, ADL domain score can be determined from corresponding sensor(s) (as shown in Table 2) to capture the relevant associated home activity(s). In particular, in this example, score for five activity domains are captured relating to mobility, hygiene, dressing, postural transfer (lying to standing), and preparing meals. For each activity, a score is computed that will be used later to calculate ADL correlations with health and wellbeing status to output a holistic ADL score.

TABLE 2

| Activity | Motion | Power | Temperature/ Humidity | Accelerometer | Circuit meter | Reed switch |
| --- | --- | --- | --- | --- | --- | --- |
| Mobility | ✓ | | | | | |
| Hygiene | ✓ | | ✓ | | | |
| Dressing/ Grooming | ✓ | | | | | ✓ |
| Transfer | ✓ | | | ✓ | | |
| Meal | ✓ | ✓ | | | ✓ | ✓ |

Examples of the calculation of domain scores will now be described in more detail for each domain, with reference to the domain scores shown in FIGS. 9A to 9F and sensor readings shown in FIGS. 10A to 10E.

Mobility

Figure 10A:
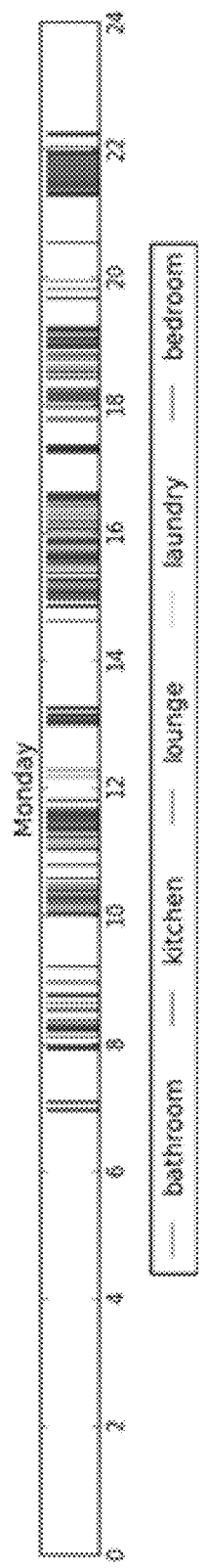
FIG. 10A is a schematic diagram of an example of motion sensor firings.

Daily indoor steps are computer to reflect the mobility status of the resident. This involves only motion sensors deployed at every room of the house. FIG. 10A shows an example of motion sensor firings from different rooms, represented in different colours of spikes over a day.

This information is then used to compute steps between rooms from consecutive firings between two motion sensors in different rooms as shown in Table 3.

TABLE 3

| Steps | Dining room | Lounge | Kitchen | Laundry | Bedroom | Bathroom |
| --- | --- | --- | --- | --- | --- | --- |
| Dining room | 0 | 5 | 10 | 9 | 13 | 12 |
| Lounge | 5 | 0 | 8 | 4 | 8 | 7 |
| Kitchen | 10 | 8 | 0 | 10 | 16 | 15 |
| Laundry | 9 | 4 | 10 | 0 | 6 | 4 |
| Bedroom | 13 | 8 | 16 | 6 | 0 | 5 |
| Bathroom | 12 | 7 | 15 | 4 | 5 | 0 |

Together with motion sensor firings, this is used to conclude the indoor steps as a score to represent indoor mobility status, as shown in Equation (2).

$$\text{Mobility} = \Sigma_{i,j} \text{Steps}(Room_i, Room_j) * (Motion_i - Motion_j) \qquad (2)$$

Although this approach is not as accurate as that of a step count wearable pedometer, this assessment is based on a relative change of an individual's indoor mobility status rather than accurate, absolute daily steps. Therefore, mobility calculated from motion sensors is sufficient to reflect to reflect change based on their estimated indoor activities.

Figure 9A:
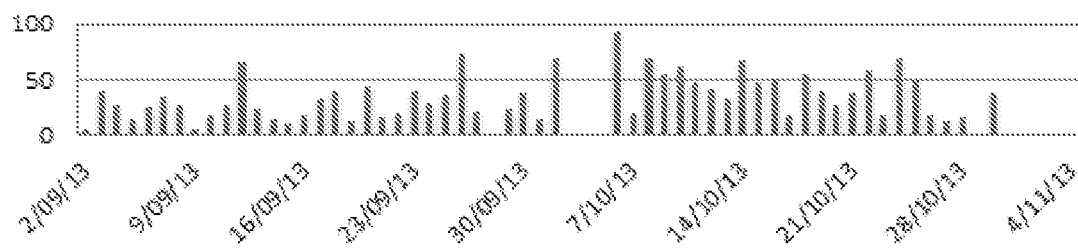
FIGS. 9A to 9F are graphs showing examples of different domain scores over time.

An example of a derived mobility score is shown in FIG. 9A.

Hygiene

Figure 10B:
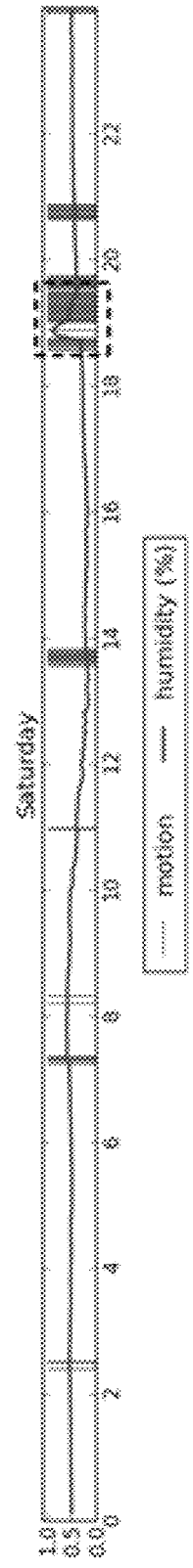
FIG. 10B is a schematic diagram of an example of humidity value changes in a bathroom.

This activity represents how well the subject maintains hygiene status, inferred through bathroom usages. Hygiene scores thus can be calculated through changes of humidity readings from the temperature/humidity sensor deployed in the bathroom, together with the bathroom motion sensor. From humidity changes, it is easy to determine bathroom usages such as taking showers, as illustrated in FIG. 10B, around 19:00.

To correctly compute hygiene scores, it is necessary to consider both bathroom motion sensor readings and humidity changes as shown in Equation (3).

$$\text{Hygiene} = \Sigma_{t=0}^{23:59:59} |Humidity_{t+1} - Humidity_t| * Motion_t \qquad (3)$$

Figure 9B:
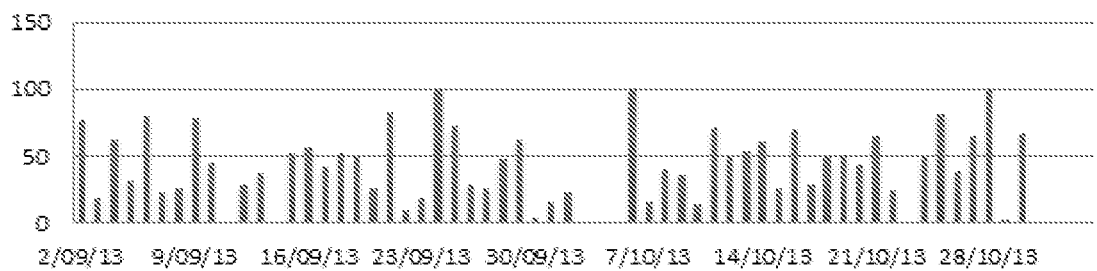

An example of daily hygiene score corresponding to washroom/bathroom inferred showering activity is shown in FIG. 9B. This could also be further confirmed by additional sensors, such as flow sensors, vibration sensors or the like, to differentiate different taps being used.

Dressing

A contact sensor, such as a reed switch is attached to the door of a bedroom wardrobe, and thus can infer dress activity through state changes of the reed switch and bedroom motion sensor in Equation (4).

$$\text{Dress} = \Sigma_{t=0}^{23:59:59} Reed_t * Motion_t \qquad (4)$$

Figure 9C:
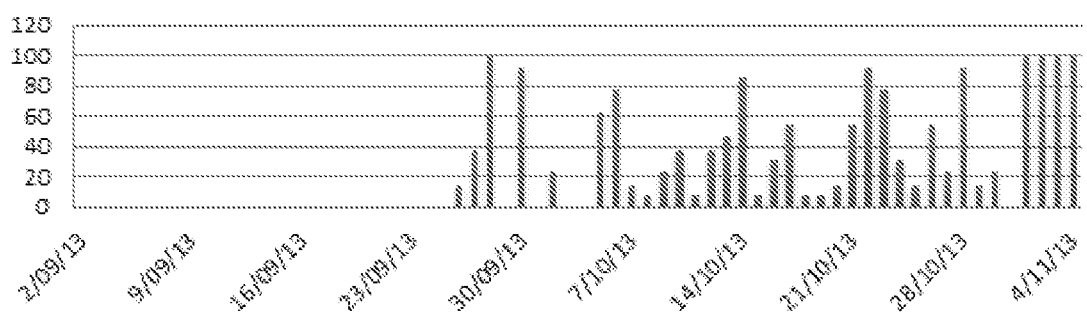

An example of daily dressing activity is shown in FIG. 9C.

Transfer

Figure 10C:
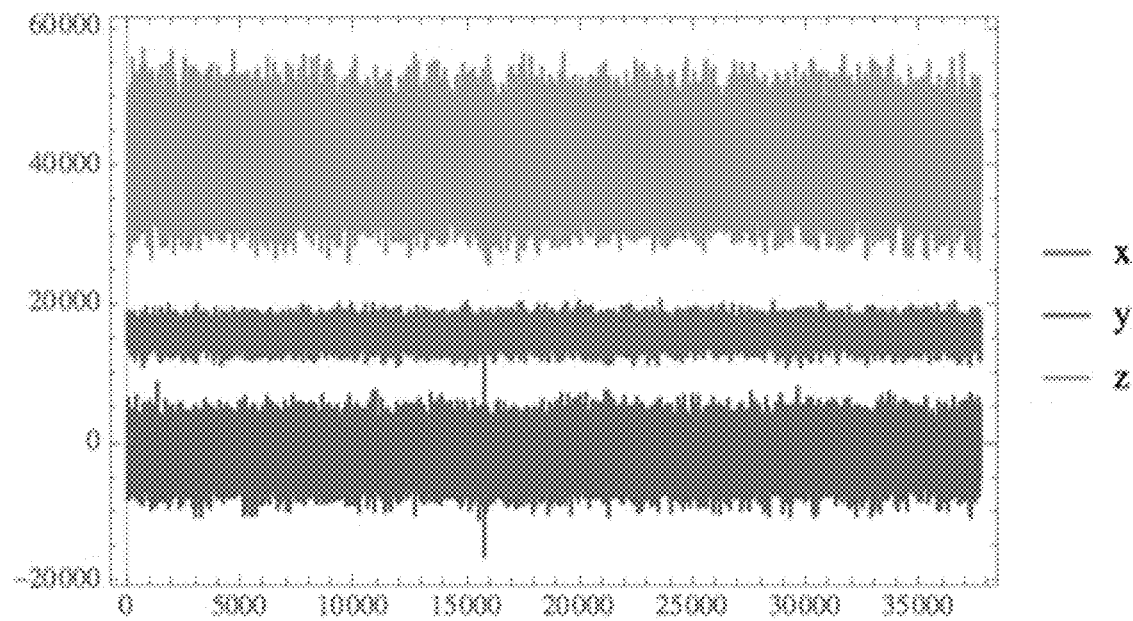
FIG. 10C is an example of accelerometer readings from an individual's bed.
Figure 10D:
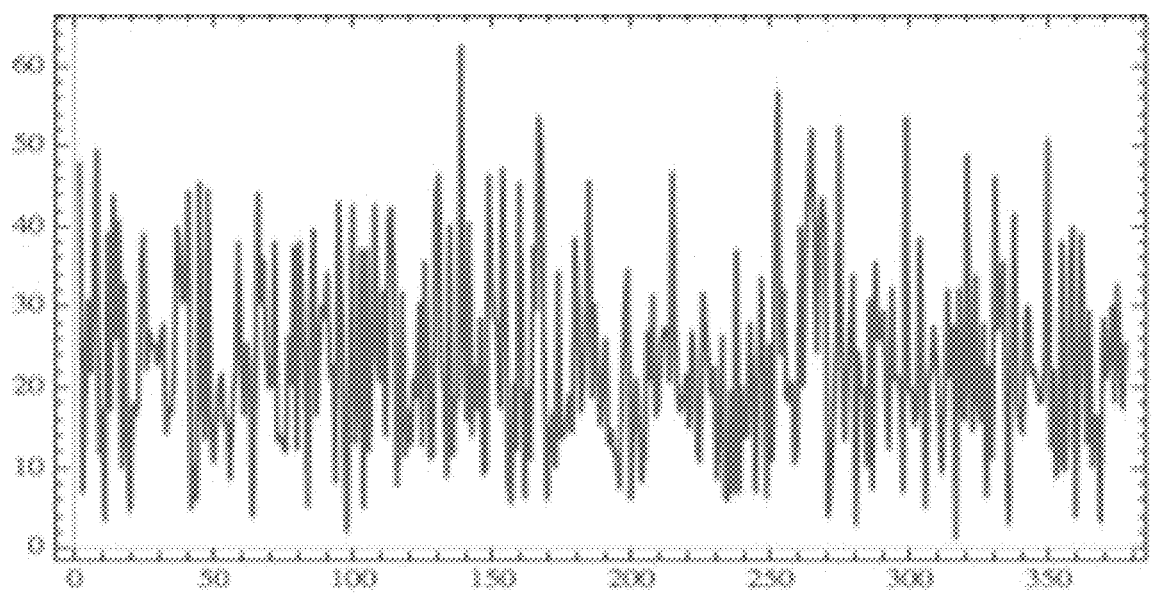
FIG. 10D is an example of accelerometer angle changes indicative of bed movements.

Postural transfers related to lying to standing and vice-versa are measured from integrated information collected from bedroom motion sensor and accelerometers. The bedroom motion sensor can be used to indicate when bedroom is occupied during a day. The 3-axis accelerometer attached to the bed mattress, detects bed vibrations during sleep and get up from/lie down on bed. FIG. 10C shows original 1 Hz vibration data from accelerometer of one night's sleep.

Considering the bed movement at every time point as a three-dimensional vector, $\vec{v}(x, y, z)$, it is possible to compute the angles between vectors and thus detect bed postural transfer automatically by counting the occurrence of torso inclination angles to lower limb. For instance, in FIG. 10D, there are 4 postural transfer detected if a threshold of inclination angle is set to 52°.

Thus, the transfer score can be computed using equation (5):

$$\text{Transfer} = \Sigma \text{Angle} \geq \text{threshold} \quad (5)$$

It would be noted that the value of inclination angle threshold will differ among different individuals, and would therefore typically need to be assessed during the baseline time period.

Figure 9D:
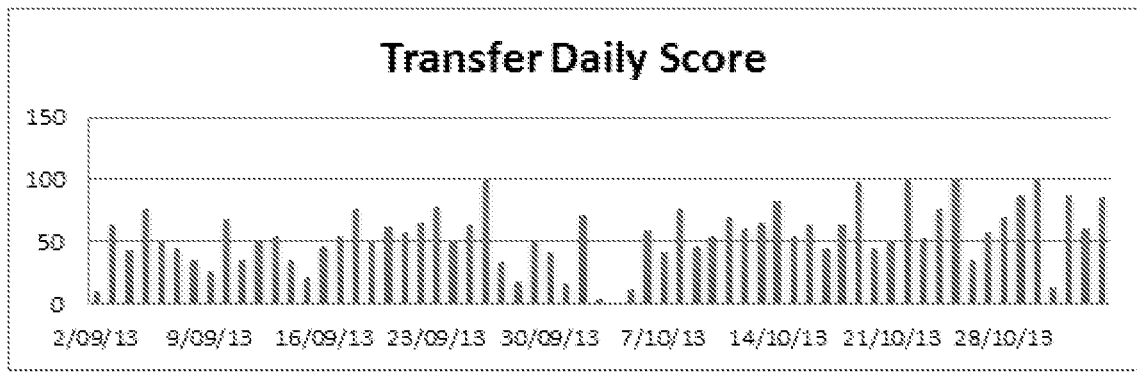

An example of a resulting daily transfer activity score corresponding to posture transfer tasks from state of lying in bed to getting up is shown in FIG. 9D.

Section 3.5 Meal

Figure 10E:
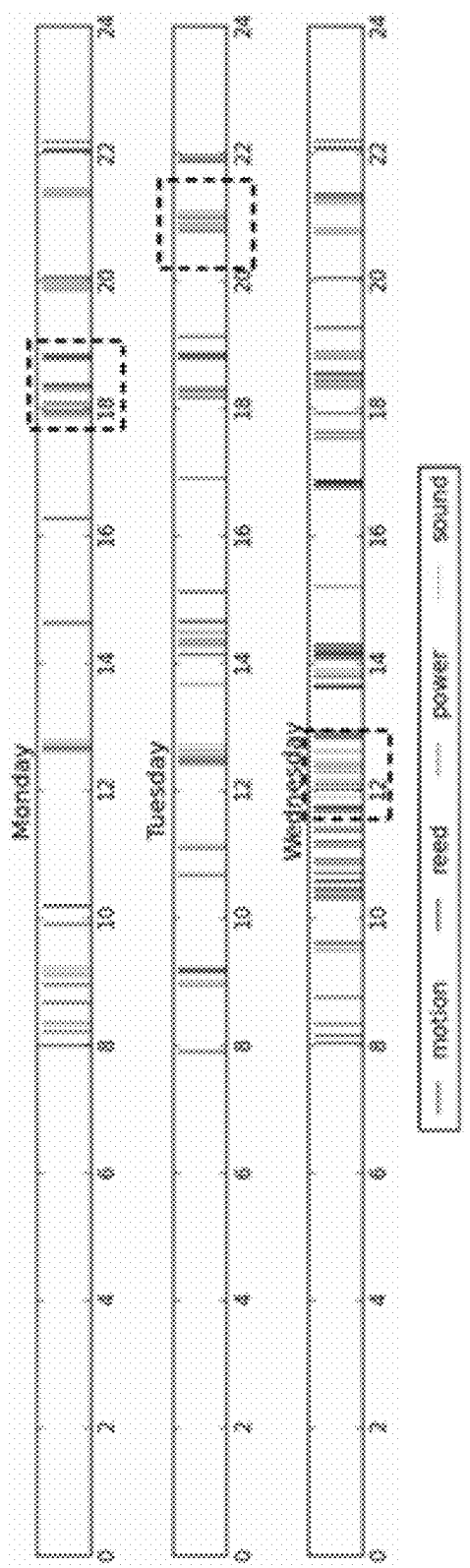
FIG. 10E is a schematic diagram indicative of sensor firing associated with meal preparation.

Extracting meal activity can be difficult as preparing a meal typically involves multiple actions. Data from multiple sensors placed in the kitchen thus need to be gathered collectively to infer a meal activity. FIG. 10E illustrates three days sensor firings for all meal preparation related sensors in a home.

In order to more accurately identify meal preparation, clustering techniques are used to extract the meal preparing activities from related sensor data, based on an assumption that meal preparation will normally involve related sensor firings in a short time period. By assigning various probabilities of sensors related to meal activity, it is possible to compute blocks of time periods of meal preparation with high probability, as illustrated by boxes in FIG. 10D.

Using this configuration, a meal score can be derived using equation (6):

$$\text{Meal} = \Sigma_{i=1}^{number\ of\ meals} \Sigma_{j \in Related\ Sensors} Pr(j) \quad (6)$$

Figure 9E:
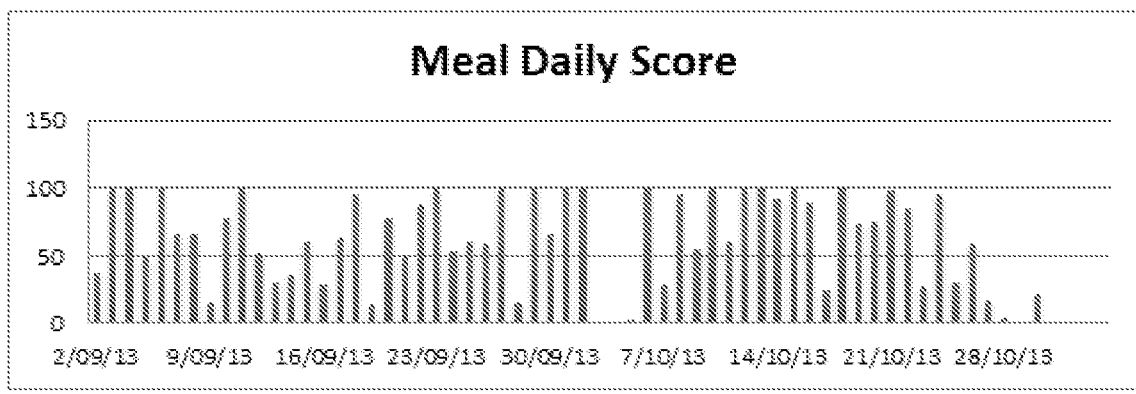
Figure 9F:
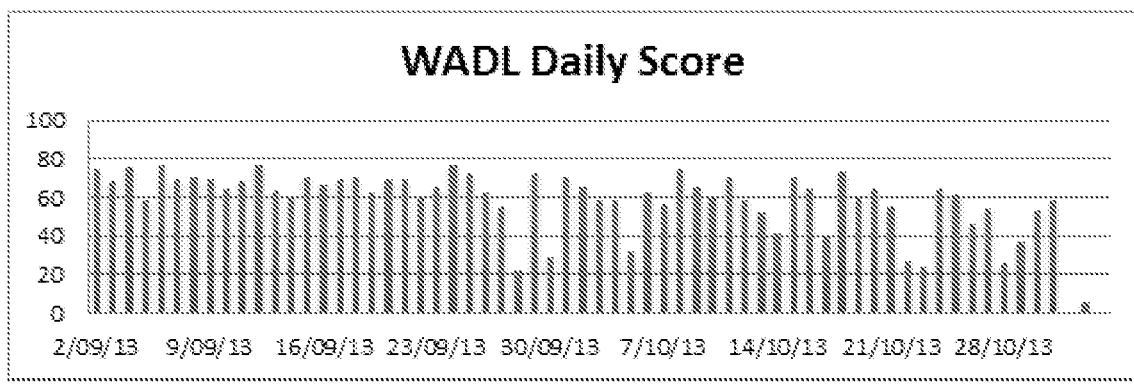

An example of daily meal preparation activity scores corresponding to cluster of kitchen activities that constitute to major meal activities are shown in FIG. 9E.

Objective Assessment of ADL Scores

In a typical assessment conducted in a clinical setting, ADL is scored in binary (0/1) from which the aggregated score equates to a functional independence score. As the functional assessment is conducted in an artificial setting, it is unreflective on the type or frequency or duration of home activities that a subject is likely to perform daily and hence contribute to the ADL domains that correspond to the health and wellbeing. Hence, the current system derives an ADL score to reflect one's daily home activities that can then be compared against baseline, typically measured for a healthy state of the individual's wellbeing.

To use objective ADL scores to reflect health and wellbeing status of an individual, it is necessary to demonstrate that activity measurements acquired through environmental sensors can be effectively correlated with physiological (if related to illness that relates to a decline in measurement e.g. blood pressure or body temperature) or physical (gathered by resident's perception) decline.

To achieve this, data were collected and then a comparison performed between the objective ADL measure and standard subjective techniques.

To achieve better regression results, raw ADL values are normalized by computing Z-scores:

$$ADL = \frac{ADL - \text{Mean}\ (ADL)}{Std(ADL)} \quad (7)$$

Figure 11A:
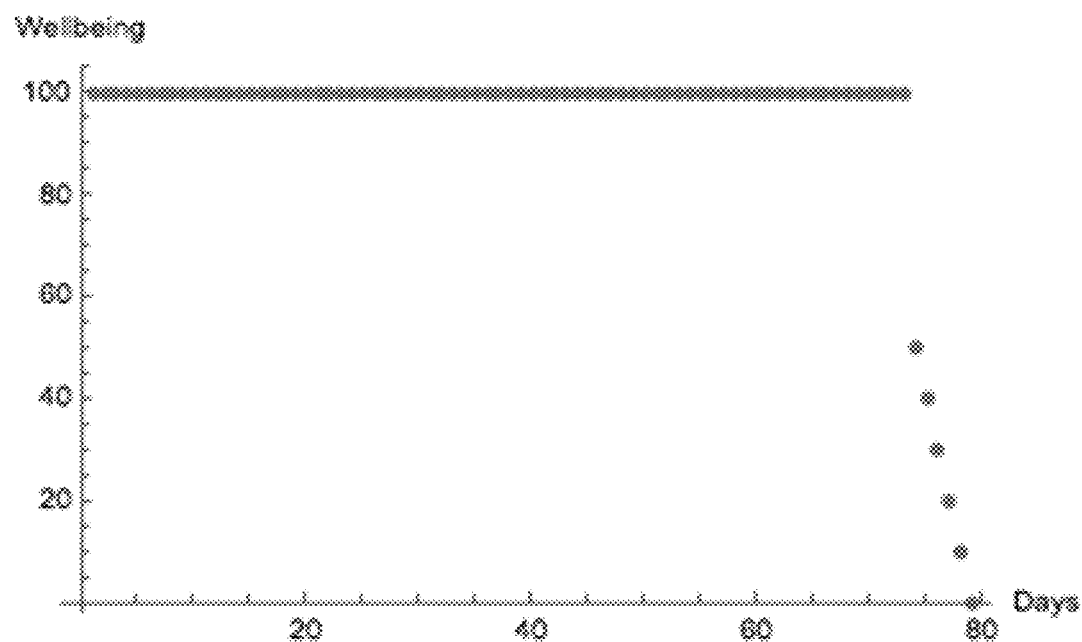
FIG. 11A is a schematic diagram of wellbeing scores.

To find correlations between ADLs and daily wellbeing, weekly questionnaires and self-report dairies were provided to a number of subjects to understand their daily wellbeing. FIG. 11A shows continuous 80 days wellbeing scores of a resident from her self-reports and medical records, with 0 representing a very bad day and 100 representing a very good day. It will be noted that in this instance wellbeing started dropping on Day 75 reaching 0 in Day 80. This was later noted to be due to the resident being subjected to a sudden event of neurological decline in Day 75, and eventually resulted in the resident hospitalized on day 81.

Figure 11B:
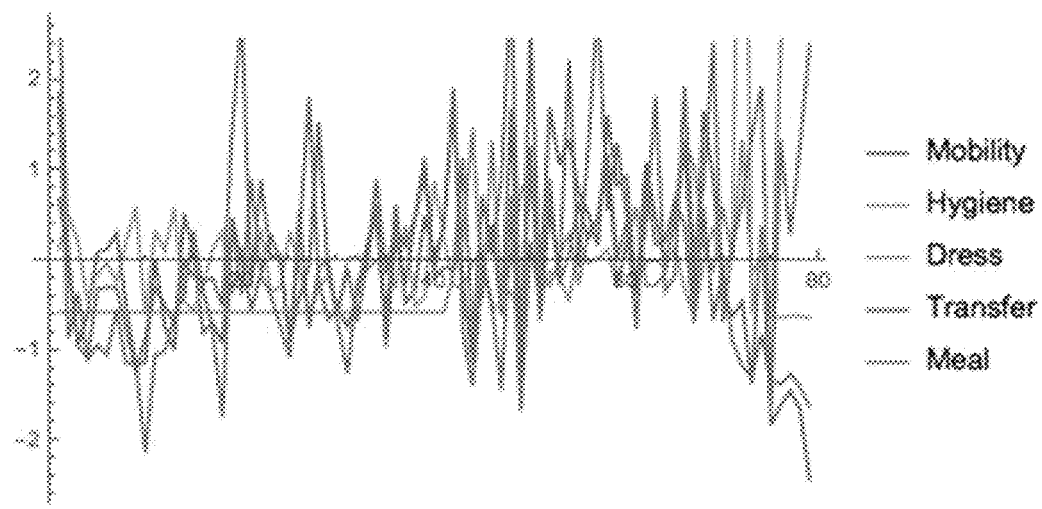
FIG. 11B is a graph illustrating domain scores for an individual.

Rescaled ADLs measured through this time period are shown in FIG. 11B. During the last week, due to neurological decline event, the subject's home activities were confined to the bedroom where the subject was found to be inactive. That is why the bedroom related activities, i.e. Dress and Transfer, have higher values. In the same time, other activities, i.e. Mobility, Hygiene, Meal, dropped significantly.

Pairwise correlation to minimize harmful effects of multicolinearity are shown in Table 4.

TABLE 4

|  | Mobility | Hygiene | Dress | Transfer | Meal |
|---|---|---|---|---|---|
| Mobility | 1 | .04 | −.23 | .38 | .6 |
| Hygiene |  | 1 | .03 | .05 | −.09 |
| Dress |  |  | 1 | .35 | −.22 |
| Transfer |  |  |  | 1 | .11 |
| Meal |  |  |  |  | 1 |

Because no two activities show strong linear correlations, all activities of this subject were used to compute ADL scores. Specifically multivariate linear regression model was used to derive ADL scores from daily activities, as shown in equation (8) and (9):

$$ADL_0 = a_0 + \Sigma_{i=1}^n a_i * \text{Activity}_i \quad (8)$$

$$ADL_0 = a_0 + a_1 \cdot \text{Mobility} + a_2 \cdot \text{Hygiene} + a_3 \cdot \text{Dress} + a_4 \cdot \text{Transfer} + a_5 \cdot \text{Meal} \quad (9)$$

Table 5 lists coefficients computed to reflect on the weighted influence of specific ADL domains towards the overall ADL score from daily activity data of the subject.

TABLE 5

|  | $a_0$ | $a_1$ | $a_2$ | $a_3$ | $a_4$ | $a_5$ |
|---|---|---|---|---|---|---|
| Coefficients | 94** | 7.3** | 3.6** | −11.2** | −5.3** | 1.8 |

The weighted ADL score for this subject, according to their ADL domains, is therefore:

$$ADL_0 = 94 + 7.3 \cdot \text{Mobility} + 3.6 \cdot \text{Hygiene} - 11.2 \cdot \text{Dress} - 5.4 \cdot \text{Transfer} + 1.8 \cdot \text{Meal} \quad (10)$$

In this subject, increase in ADL domains Dressing and Transfer reflect negatively on their health and wellbeing status. Dressing, however, may be skewed by the wardrobe being left open and the contact sensor not reflecting accurately of accessing clothes only when there is an activity of dressing. It will also be appreciated however that this can be obviated by knowing if the individual leaves the wardrobe open as habit, and hence taken into account by measurements collected during the reference time period.

The ADL score over the 9 weeks leading to the subject's neurological event is shown clearly as fluctuations of ADL score over the last 3 weeks in FIG. 11B.

Representations

Figure 12A:
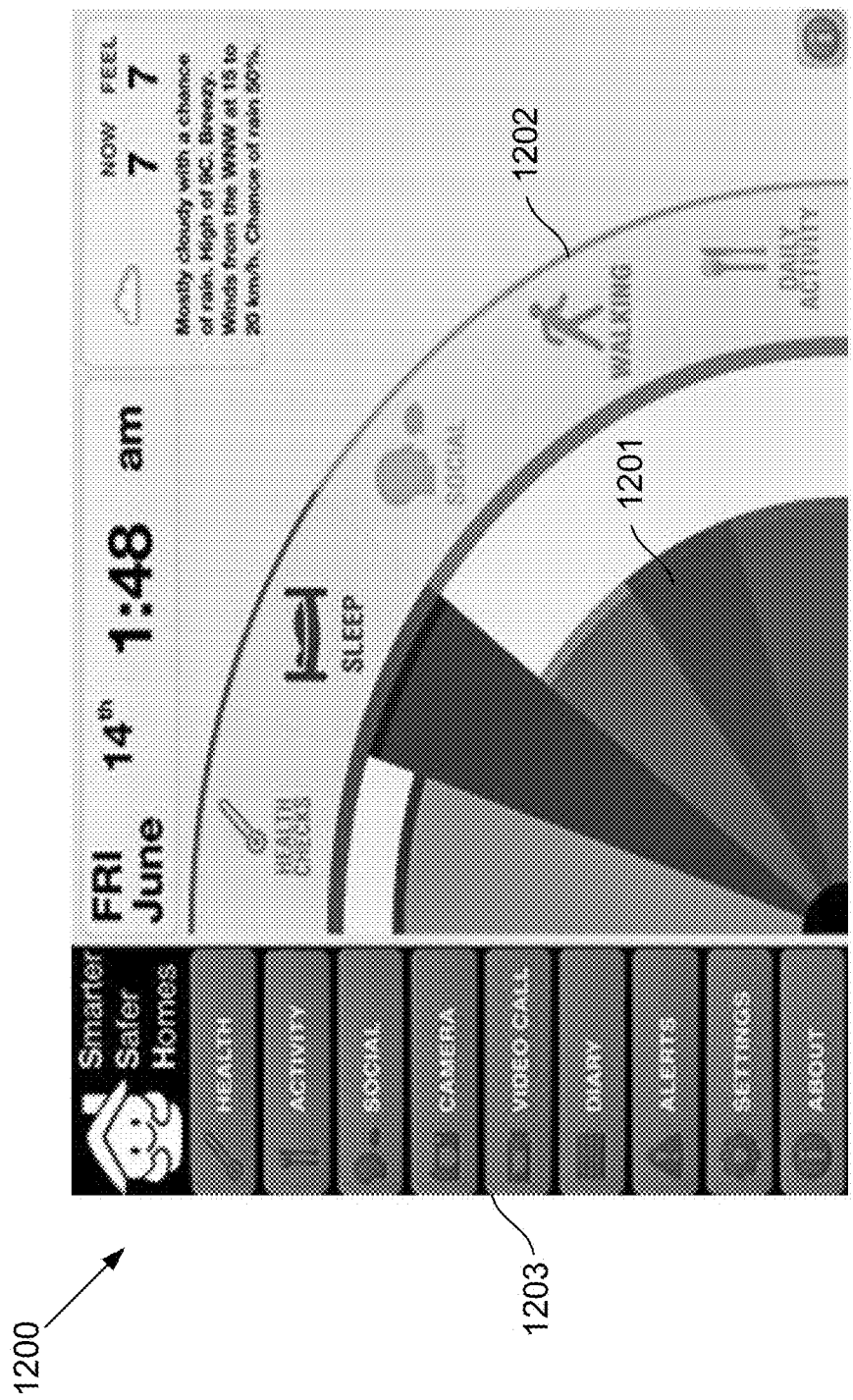
FIGS. 12A to 12C are schematic diagrams of example of user interfaces.
Figure 12B:
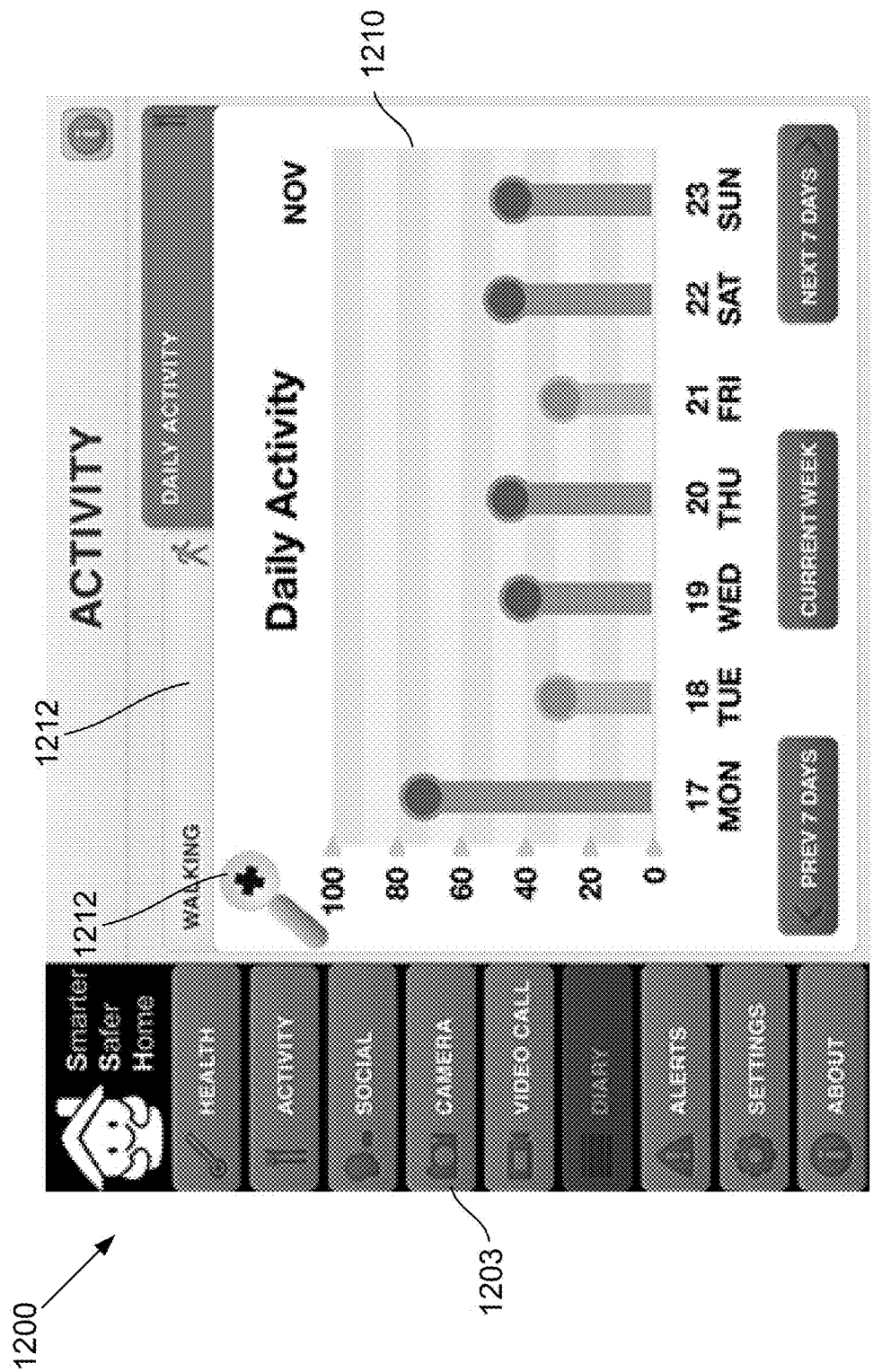
Figure 12C:
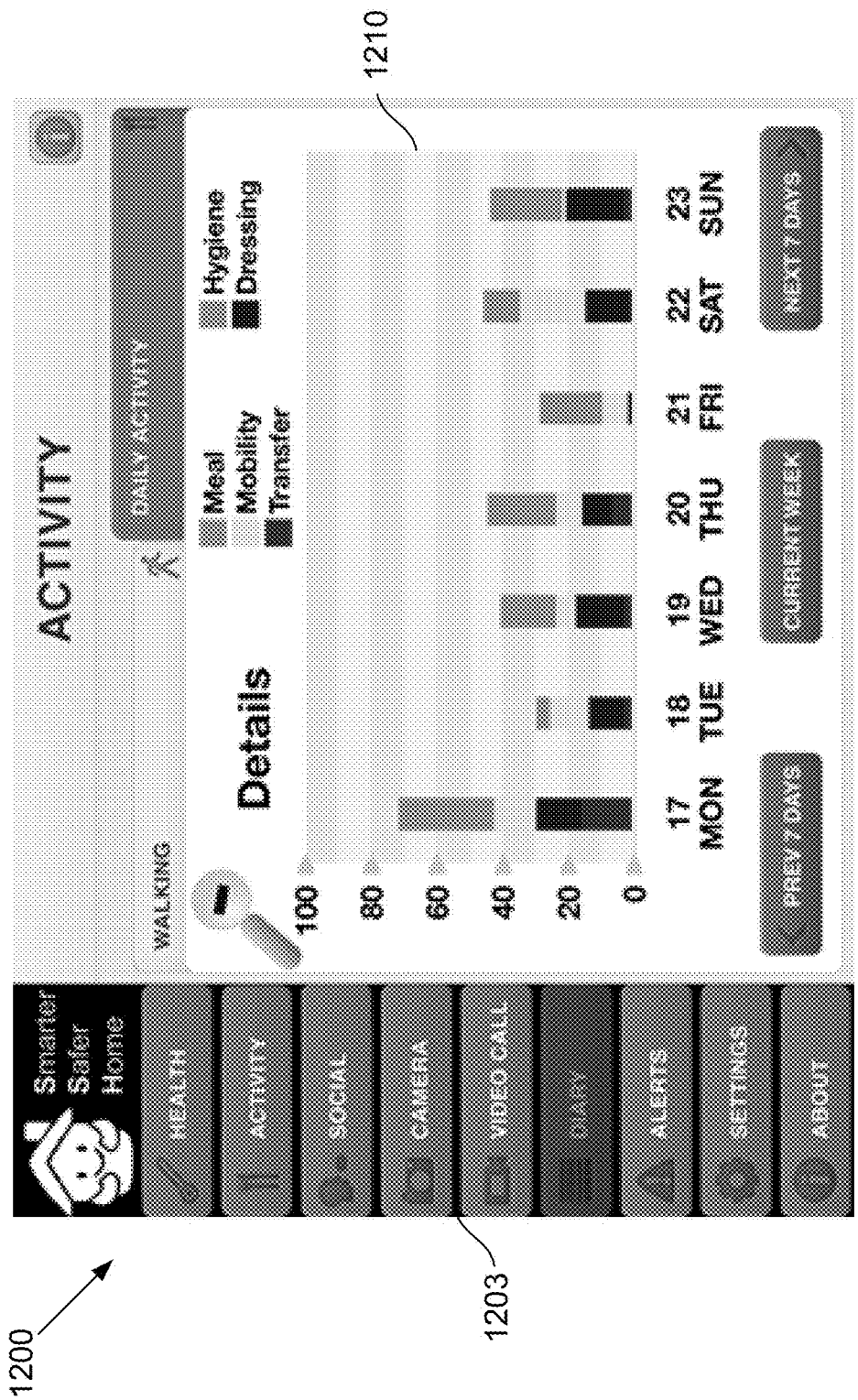

To promote self-monitoring and easily understand of results, graphical representation of resulting ADL scores can be used, and examples of these are shown in FIGS. 12A to 12C.

In the dashboard representation 1200 shown in FIG. 12A, coloured rays 1201 are used to represent the domain score associated with each of the five domains 1202, with the length of each ray representing a grading score of health and wellbeing parameters relevant to functional independence including the mobility domain and overall score of ADL, with each grading score being compared against a respective baseline or reference score.

Selecting an "activity" option presented in the menu 1203 allows the user to view details of daily activities, as shown in FIG. 12B. In this example, the dashboard representation 1200 includes a graph 1210 of ADL scores calculated using the linear regression formula discussed above, for a specific activity shown on tab 1211. The scores can be colour coded, for example using a traffic light scheme representing a good, below average and bad functional capability, with good days being shown for Mon, Wed, Thu, Sat and Sun, and below average days shown for Tue and Fri, in this example.

Moreover, by tapping the magnifying glass 1212, uses can zoom in to see further details of scores of normalized activities, as shown in FIG. 12C. This representation gives an easy-to-understand visual impressions of how ADL score is computed, showing the score for each segmented into subject ADL domains. For instance, if we take Monday as a normal good day of functional capability, then this day can be used as a signature pattern particularly related to this individual. For Tuesday and Friday, the big variation of their patterns from the signature pattern will explain why domains have led ADL scores in amber.

Accordingly, the above described system and method provides an objective assessment/measure of ADL specific to a subject's own living profile, including the environment in which they live. In one example, an activity level indicator (also referred to as an ADL score) is determined based on sensor readings obtained from sensors placed within the subject's living environment and which are consequently non-intrusive. Furthermore, the resulting ADL score can be compared to a baseline score calculated within the individual's own living environment, which therefore allows this to represent changes in the individual's activity capabilities, as reflected by their everyday living routines.

Thus, this provides an objective assessment of ADL in a setting representative of the person's living environment. By using sensor data collected from sensors in the subject's environment, this ensures the assessment is objective and reflective of the subject's normal course of daily activities and interactions in their own living setting. This would be more reflective of a functional capacity pertaining to the subject's own self-profile, and avoids the need for subjective assessment, either by the individual themselves, or by medical practitioners, or other specialised personnel.

Furthermore, this not only improves the determination of change/progress through time the ADL from a subject's own benchmark (baseline) but also provide a more regular assessment for their family and carrier to have increased and timely access to act on any early decline in function. Thus, a more timely assistance or intervention can be undertaken.

Compared with existing methods, this provides a more consistent approach and is reflective of human visual assessment and of their living environment, respectively. This approach is also less intrusive psychologically (once they become comfortable with the sensors in their environment) that it is less instructive and aligned to their lifestyle activities.

Thus, in comparison with previous techniques, the current technique determines an activity indicator measured in an objective and continuous manner, which as a result is more likely to be more consistent and accurate. Unlike the assessment performed simulated in a clinical setting, the activity indicator is based on the individual's own living environment and also referenced to one's functional state, and therefore, changes in the activity indicator would be more reflective and representative to the subject's activity profile and health status.

Unlike methods that involve using wearable or visual sensor systems to derive measures of ADL, the ADL in this invention derived from non-intrusive sensors placed around the subject's living environment therefore placing less burden of added daily task and/or interaction with technology to achieve. Furthermore, this allows detection based on various activity patterns reflective of day-to-day health status, forming a much more integrated with their physiological and somewhat psychological condition.

Automatic determination of ADLs enables objective assessment of functional independence, particularly in a home environment for the elderly people living independently. These ADL scores can be used to support older people living alone in self-management of their functional independence; and simultaneously provide the capacity for family members to provide better support to their elderly parents living alone remotely. Furthermore, an automated ADL assessment feature could also provide health care providers the capacity to monitor older peoples' health care status more regularly, and provide a more timely and early intervention through telehealth. The techniques could be applied to numerous different scenarios, including but not limited to:

Assessment of older people in their functional independent assessment and wellbeing;

Early Intervention to provide assistive technologies in people losing their functional ability to live independently;

Early intervention of care assistance to support the limited functional capability or disability;

As in above, people with disability could be supported similarly;

A parent needing to watch their teenage kids in the home should they occasionally need to go out to attend to activities like shopping;

Efficiency of work environment e.g. Nursing service attending to institutional care setting to determine resource allocation;

Behavioural mapping for subject assessment and needs;

Behavioural mapping that represent any psychological decline;

Resident care monitoring and focused care to the needed resident;

Contribute to other ADL index measurements such as Barthel index; and,

Contribute to assessment instruments e.g. ACAT, determining eligibility or prevention to residential care facility.

The term "subject" will be understood to include a patient or other individual that is being monitored.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A method of monitoring activity capabilities of a subject, the method including, in at least one processing device:
   a) determining sensor data indicative of sensor readings for each of a plurality of sensors, the sensors being mounted in a living environment of the subject and the sensor data for each sensor being at least partially indicative of one or more activities performed by the subject;
   b) for each of a plurality of activity domains, determining a domain score indicative of a level of activity within the respective activity domain, the domain score being determined using sensor data from a respective combination of sensors associated with the respective domain, wherein the activity domains are activities of daily living (ADL) domains including:
      i) hygiene;
      ii) meal preparation;
      iii) mobility;
      iv) transfer; and
      v) dressing;
   c) determining a reference activity level using reference domain scores measured during a reference time period, wherein the reference domain scores are determined using the sensor data from the sensors mounted in the living environment of the subject during a reference time period;
   d) determining a current activity level using current domain scores measured during a monitoring time period;
   e) generating an activity indicator at least partially in accordance with the current activity level and the reference activity level, the activity indicator being at least partially indicative of differences between the current activity level and the reference activity level, thereby providing feedback on the activity capabilities of the subject;
   f) comparing the current activity level to the reference activity level that is measured during the reference time period, such that the current activity level as measured on a given day is compared to a reference activity level established for the same day during the reference time period; and,
   g) determining an activity level score based on results of comparing the current activity level to the reference activity level, wherein the activity level score is a single numerical overall score indicating a functional independence of the subject with regard to the ADL domains.

2. A method according to claim 1, wherein the method includes:
   a) determining the reference activity level using the activity level score measured during the reference time period; and,
   b) determining the current activity level using the activity level score measured during the monitoring time period.

3. A method according to claim 1, wherein the combination of the domain scores includes at least one of:
   a) a sum; and,
   b) a weighted sum.

4. A method according to claim 3, wherein the weighted sum includes applying different weightings to different domain scores based on a degree of priority, relevance or severity of a condition of the subject.

5. A method according to claim 1, wherein the method includes:
   a) determining an activity pattern indicative of relative values of domain scores;
   b) determining the reference activity level using the activity pattern measured during the reference time period; and,
   c) determining a current activity level using a current activity pattern measured during the monitoring time period.

6. A method according to claim 1, wherein the method includes:
   a) comparing the current activity level to the reference activity level; and,
   b) generating the activity indicator at least partially in accordance with results of the comparison.

7. A method according to claim 6, wherein the method includes comparing at least one of:
   a) each current domain score to an equivalent reference domain score of the subject;
   b) each current domain score to a respective reference range derived from an equivalent reference domain score of the subject;
   c) a current activity level score to a reference activity level score of the subject;
   d) a current activity level score to a respective reference range derived from a reference activity level score of the subject;
   e) a current activity pattern to a reference activity pattern of the subject; and,
   f) a current activity level to a reference activity level of the subject measured during a corresponding time period.

8. A method according to claim 7, wherein the method includes:
   a) determining a condition suffered by the subject; and,
   b) determining, at least partially in accordance with the condition, at least one of:
      i) an activity level score;
      ii) a domain score;
      iii) a reference domain score range; and,
      iv) a reference activity level range.

9. A method according to claim 6, wherein the method includes:
   a) determining an action rule; and,
   b) selectively performing an action in accordance with the action rule and in response to the results of the comparison, wherein the action includes:
      i) generating an alert notification; and,
      ii) providing the alert notification to a user by transferring the alert notification to a client device of the user via a communications network.

10. A method according to claim 1, wherein the method includes:
a) generating a representation indicative of at least one of:
i) results of a comparison;
ii) current domain scores;
iii) reference domain scores;
iv) current activity level scores;
v) reference activity level scores;
vi) current activity level patterns;
vii) reference activity level patterns; and,
viii) the activity indicator; and,
b) providing the representation to a client device via a communications network.

11. A method according to claim 1, wherein the method includes determining a domain score using sensor data from a respective combination of sensors, and wherein the respective combination of sensors for each domain is determined based on at least one:
a) a sensor type; and,
b) a sensor location.

12. A method according to claim 1, wherein the sensors include at least one of:
a) motion sensors;
b) power sensors that monitor operation of appliances;
c) temperature sensors;
d) humidity sensors;
e) accelerometers; and,
f) door sensors.

13. A method according to claim 1, wherein the method includes, for at least one domain:
a) identifying events using sensor data from the sensors, wherein identifying the events includes comparing sensor data to a number of signatures, each signature being indicative of a respective event; and,
b) determining the domain score using at least one of:
i) a sum of a number of events during a time period; and,
ii) a sum of a number of clusters of events during a time period.

14. A method according to claim 1, wherein the method further includes prioritizing at least one domain over at least another domain for the subject in calculating the activity level score.

15. A method according to claim 1, wherein the method further includes comparing an activity level score to a range established using reference activity levels, the range being restricted to at least one domain prioritized over at least another domain.

16. An apparatus for monitoring activity capabilities of a subject, the apparatus including:
a) a plurality of sensors, the sensors being mounted in a living environment of the subject; and,
b) at least one processing device that:
i) determines sensor data indicative of sensor readings for each of the plurality of sensors, the sensor data for each sensor being at least partially indicative of one or more activities performed by the subject;
ii) for each of a plurality of activity domains, determines a domain score indicative of a level of activity within the respective activity domain, the domain score being determined using sensor data from a respective combination of sensors associated with the respective domain, wherein the activity domains are activities of daily living (ADL) domains including:
(1) hygiene;
(2) meal preparation;
(3) mobility;
(4) transfer; and
(5) dressing/grooming;
iii) determines a reference activity level using reference domain scores, wherein the reference domain scores are determined using the sensor data from the sensors mounted in the living environment of the subject during a reference time period;
iv) determines a current activity level using current domain scores measured during a monitoring time period;
v) generates an activity indicator at least partially in accordance with the current activity level and the reference activity level, the activity indicator being at least partially indicative of differences between the current activity level and the reference activity level, thereby providing feedback on the activity capabilities of the subject;
vi) compares the current activity level to a reference activity level that is measured during the reference time period, such that the current activity level as measured on a given day is compared to a reference activity level established for the same day during the reference time period; and,
vii) determines an activity level score based on results of comparing the current activity level to the reference activity level, wherein the activity level score is a single numerical overall score indicating a functional independence of the subject with regard to the ADL domains.

17. The apparatus according to claim 16, wherein the apparatus includes a hub provided in the living environment, the hub being adapted to communicate with each of the sensors and provide the sensor data to the at least one processing device, via a communications network.

18. The apparatus according to claim 17, wherein the apparatus includes a processing system including at least one processing device, the processing system communicating with one or more client devices via communications network, to at least one of:
a) provide alert notifications to the client devices; and,
b) allow the client devices to display a representation indicative of at least one of:
i) results of a comparison;
ii) current domain scores;
iii) reference domain scores;
iv) current activity level scores;
v) reference activity level scores;
vi) current activity level patterns;
vii) reference activity level patterns; and,
viii) the activity indicator.

* * * * *